(12) United States Patent
Hosokawa et al.

(10) Patent No.: US 11,289,191 B2
(45) Date of Patent: Mar. 29, 2022

(54) TERMINAL DEVICE AND PROGRAM

(71) Applicant: Paramount Bed Co., Ltd., Tokyo (JP)

(72) Inventors: Yuji Hosokawa, Tokyo (JP); Masato Shimokawa, Tokyo (JP); Tomoki Yoshida, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 154 days.

(21) Appl. No.: 16/485,269

(22) PCT Filed: Apr. 6, 2018

(86) PCT No.: PCT/JP2018/014709
§ 371 (c)(1),
(2) Date: Aug. 12, 2019

(87) PCT Pub. No.: WO2019/044022
PCT Pub. Date: Mar. 7, 2019

(65) Prior Publication Data
US 2019/0378612 A1 Dec. 12, 2019

(30) Foreign Application Priority Data
Aug. 30, 2017 (JP) .............................. JP2017-165536

(51) Int. Cl.
*G16H 40/63* (2018.01)
*A61G 5/10* (2006.01)
(Continued)

(52) U.S. Cl.
CPC ........... *G16H 40/63* (2018.01); *A61G 5/1059* (2013.01); *A61G 5/1067* (2013.01); *A61G 7/018* (2013.01); *G06F 3/0482* (2013.01); *G06F 3/147* (2013.01)

(58) Field of Classification Search
CPC .... G16H 40/63; A61G 5/1059; A61G 5/1067; A61G 7/018; G06F 3/0482; G06F 3/147
(Continued)

(56) References Cited

U.S. PATENT DOCUMENTS 7,690,059 B2 * 4/2010 Lemire ................ A61G 7/0506
5/600
9,066,602 B2 * 6/2015 Rawls-Meehan ...... G05B 15/02
(Continued)

FOREIGN PATENT DOCUMENTS

DE  102016102752 A1  9/2016
JP  2004-141484 A  5/2004
(Continued)

OTHER PUBLICATIONS

International Search Report PCT/ISA/210 for International Application No. PCT/JP2018/014709 dated Jul. 10, 2018.
(Continued)

*Primary Examiner* — William D Titcomb
(74) *Attorney, Agent, or Firm* — Harness, Dickey & Pierce, P.L.C.

(57) ABSTRACT

An embodiment of the invention is a terminal device controlling a body support apparatus capable of a first operation and a second operation; the terminal device includes a displayer and a controller; the displayer displays an operator controlling an operation of the body support apparatus; the controller switches between a first display format and a second display format based on an instruction from an outside; the first display format displays a first operator and a second operator in the displayer; the first operator controls the first operation; the second operator controls the second operation; and the second display format displays one of the first operator or the second operator in the displayer.

12 Claims, 23 Drawing Sheets

(51) Int. Cl.
*A61G 7/018* (2006.01)
*G06F 3/0482* (2013.01)
*G06F 3/147* (2006.01)

(58) Field of Classification Search
USPC .......................................................... 702/19
See application file for complete search history.

(56) References Cited

U.S. PATENT DOCUMENTS

| | | | | |
|---|---|---|---|---|
| 10,201,466 | B2* | 2/2019 | Shimada | A61G 7/005 |
| 10,413,462 | B2* | 9/2019 | Shimada | A61G 7/018 |
| 2006/0277683 | A1* | 12/2006 | Lamire | A61G 7/015 |
| | | | | 5/600 |
| 2007/0157385 | A1* | 7/2007 | Lemire | A61G 7/0509 |
| | | | | 5/600 |
| 2008/0235872 | A1* | 10/2008 | Newkirk | G06F 3/0481 |
| | | | | 5/600 |
| 2009/0151074 | A1* | 6/2009 | Nagaoka | A47C 20/041 |
| | | | | 5/616 |
| 2010/0125953 | A1* | 5/2010 | Nagaoka | A61G 7/018 |
| | | | | 5/618 |
| 2016/0120718 | A1* | 5/2016 | Shimada | A61G 7/005 |
| | | | | 5/618 |
| 2016/0270195 | A1 | 9/2016 | Ikehara et al. | |
| 2016/0331614 | A1* | 11/2016 | Furman | A61G 7/0506 |
| 2017/0112716 | A1* | 4/2017 | Rawls-Meehan | A61G 7/015 |
| 2017/0143565 | A1* | 5/2017 | Childs | A61G 7/012 |
| 2017/0172827 | A1* | 6/2017 | Schaaf | A61G 7/018 |
| 2018/0184811 | A1* | 7/2018 | Nava | A47C 17/04 |

FOREIGN PATENT DOCUMENTS

| | | |
|---|---|---|
| JP | 2010-191722 A | 9/2010 |
| JP | 2011-050446 A | 3/2011 |
| JP | 2011-162007 A | 8/2011 |
| JP | 2013-062694 A | 4/2013 |
| JP | 2013-144045 A | 7/2013 |
| JP | 2016-064293 A | 4/2016 |
| JP | 2016-076038 A | 5/2016 |
| JP | 2016-167385 A | 9/2016 |
| JP | 2016-193371 A | 11/2016 |
| JP | 2017-070352 A | 4/2017 |
| WO | WO-2014/185164 A1 | 11/2014 |

OTHER PUBLICATIONS

Written Opinion of the International Searching Authority PCT/ISA/237 for International Application No. PCT/JP2018/014709 dated Jul. 10, 2018.

* cited by examiner

| USER ID | HEAD SPEED | HEIGHT SPEED | COMBINATION ENABLEMENT | HEAD OPERATION ENABLEMENT | FOOT OPERATION ENABLEMENT | HEIGHT OPERATION ENABLEMENT | MEMORY ENABLEMENT | HEAD MEMORY | FOOT MEMORY | HEIGHT MEMORY | BED-EXIT NOTIFICATION ENABLEMENT |
|---|---|---|---|---|---|---|---|---|---|---|---|
| U0000001 | NORMAL | FAST | AUTHORIZED | AUTHORIZED | PROHIBITED | AUTHORIZED | DEACTIVATED | 30° | 30° | 20cm | ACTIVATED |
| U0000002 | NORMAL | NORMAL | AUTHORIZED | AUTHORIZED | AUTHORIZED | AUTHORIZED | ACTIVATED | 45° | 45° | 0cm | ACTIVATED |
| ... | ... | ... | ... | ... | ... | ... | ... | ... | ... | ... | ... |

FIG. 5

| USER ID | DISPLAY PATTERN |
|---------|-----------------|
| U000001 | PATTERN 1 |
| U000002 | PATTERN 2 |
| ... | ... |

| DATE/TIME | TERMINAL USER ID | BED USER ID | BED ID | OPERATION BUTTON | CONTROL COMMAND | CONTROL RESULT |
|---|---|---|---|---|---|---|
| 2017/01/23 12:00 | U000001 | P000001 | 000002 | B001 | CMD001 | 30cm, 0°, 0° |
| 2017/01/23 12:05 | U000002 | P000002 | 000004 | B003 | CMD003, CMD006 | 30cm, 30°, 20° |
| ⋮ | ⋮ | ⋮ | ⋮ | ⋮ | ⋮ | ⋮ |

TERMINAL DEVICE AND PROGRAM

TECHNICAL FIELD

The invention relates to a terminal device and a program.

The application is based upon and claims the benefit of priority from Japanese Patent Application No. 2017-165536 filed in Japan on Aug. 30, 2017; the entire contents of which are incorporated herein by reference.

BACKGROUND ART

Conventionally, to make it easier for a patient having a physical handicap to perform actions, an apparatus that supports the body of the patient and supports operations of the patient has been developed. For example, an electric bed is known in which a chair position is formed by a back section, an upper leg section, and a lower leg section being rotated by a driver (e.g., Patent Literature 1).

PRIOR ART DOCUMENTS

Patent Literature

Patent Literature 1: Japan JP-A 2016-64293 (Kokai)

SUMMARY OF INVENTION

Problem to be Solved by the Invention

However, the controller of a conventional body support apparatus includes mechanical buttons. However, considering that the users of the body support apparatus are mainly physically-handicapped patients, it is desirable for the controller of the body support apparatus to be easily operated by being matched to the body condition of the user. For this aspect, it is not realistic to interchange the mechanical buttons of the controller according to the user. Also, although it also may be considered to prepare multiple types of controllers, such a case would undesirably increase the manufacturing cost; and there is also a possibility that the controllers may be mistaken.

One object of an embodiment of the invention is to provide a terminal device and a program in which the operationability of a body support apparatus can be improved.

Also, one object of another embodiment of the invention is to provide a terminal device and a program that can provide the effects described in embodiments described below.

Means for Solving the Problem

An embodiment of the invention is a terminal device controlling a body support apparatus capable of a first operation and a second operation; the terminal device includes a displayer and a controller; the displayer displays an operator controlling an operation of the body support apparatus; the controller switches between a first display format and a second display format based on an instruction from an outside; the first display format displays a first operator and a second operator in the displayer; the first operator controls the first operation; the second operator controls the second operation; and the second display format displays one of the first operator or the second operator in the displayer.

Also, an embodiment of the invention is a program causing a computer to execute; the computer is of a terminal device controlling a body support apparatus capable of a first operation and a second operation; the program causes the computer to execute a step of displaying an operator controlling an operation of the body support apparatus, and a step of switching between a first display format and a second display format based on an instruction from an outside; the first display format displays a first operator and a second operator; the first operator controls the first operation; the second operator controls the second operation; and the second display format displays one of the first operator or the second operator.

Effects of the Invention

According to the embodiments of the invention recited above, the operationability of the body support apparatus can be improved.

BRIEF DESCRIPTION OF DRAWINGS

FIG. 5 is a figure showing the data configuration of the operation setting information according to the same embodiment.

FIG. 6 is a figure showing the data configuration of the display setting information according to the same embodiment.

FIG. 22 is a figure showing the data configuration of history information according to the same embodiment.

MODES FOR CARRYING OUT THE INVENTION

Embodiments of the invention will now be described with reference to the drawings.

First Embodiment

Figure 1:
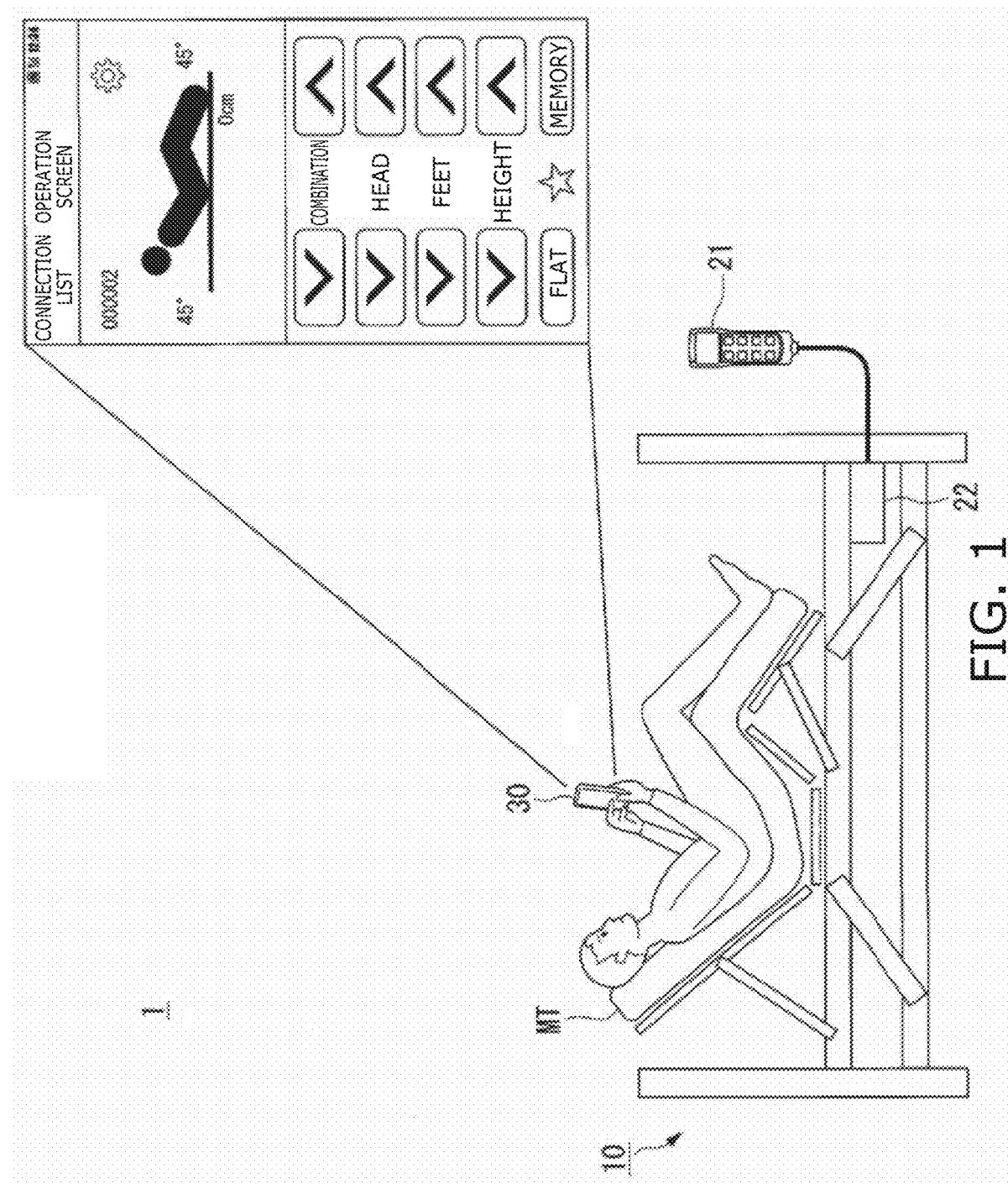
FIG. 1 is a schematic view shows an overview of a first embodiment of the invention.

FIG. 1 is a schematic view showing an overview of the embodiment.

A bed system 1 according to the embodiment includes a bed 10, a handy switch 21, a control box 22, and a terminal device 30.

The control box 22 is mounted to the bed 10 and has a wired or a wireless connection to the handy switch 21.

The bed 10 includes a driver. The bed 10 can control the raising/lowering of the height and/or the sections by the control box 22 operating the driver based on an operation instruction input by the user operating the handy switch 21.

The terminal device 30 is an electronic device including a computer system. The terminal device 30 is, for example, a device including a touch panel such as a smartphone, a tablet terminal device, a personal computer, etc. The touch panel is an electronic component in which a displayer and an inputter are configured as one body. The inputter detects the position of the contact (the touch) of a finger and/or a stylus pen on the displayer.

The touch panel can accept an operation such as a tap, a double-tap, a long-press, a flick, a pinch-in, a pinch-out, etc. A tap is an operation of touching for a short period of time. A double-tap is an operation in which a tap is performed 2 times within a prescribed period of time. A long-press is an operation of touching for a long period of time. A flick is an operation of moving the position of the touch while touching. Flicks may be differentiated by the movement direction of the position of the touch. A pinch-in is an operation in which multiple positions are touched; and the positions of the touches subsequently approach each other. A pinch-out is an operation in which multiple positions are touched; and the positions of the touches subsequently move away from each other.

Also, a program for controlling the operations of the bed 10 is installed in the terminal device 30. Thereby, the terminal device 30 operates as a remote controller of the bed 10.

In the case where the terminal device 30 operates as a remote controller, the terminal device 30 displays, on a touch panel, a control screen for accepting an instruction from the user. Operation buttons are disposed in the control screen. The operation buttons are associated with operations of the bed 10. That is, the operation buttons are examples of operators for operating the bed 10. For example, one operation button is associated with a control command of raising the height of the bed 10; and another operation button is associated with a control command of lowering the position of the lower leg section. The user of the terminal device 30 can cause the bed 10 to perform the operation associated with the operation button by touching the position where the operation button is displayed. Hereinbelow, the user of the terminal device 30 is called the terminal user. Also, hereinbelow, the user of the bed 10 is called the bed user. In the embodiment, a case is described as an example where the terminal user and the bed user are the same. Hereinbelow, the terminal user and the bed user are called simply the user when not particularly differentiating.

Here, the control screen is displayed based on setting information that is settable for each user, for each bed 10, etc. The setting information is information that determines the display mode of the operation buttons, the operation buttons to be displayed, the operation buttons not to be displayed, the operatable operation buttons, the non-operatable operation buttons, the set of the control commands corresponding to the operation buttons, the target values of the control commands corresponding to the operation buttons, etc. The display mode includes the size, the shape, the pattern, the color, and the arrangement.

Thereby, the terminal device 30 can display different control screens according to the user or according to the bed 10 to be controlled. For example, a control screen in which the operation buttons are disposed on the left side is displayed for a user having a handicapped right hand. Thereby, the operation is easy even when using only the left hand because the operation buttons are disposed in a range reached by the thumb of the left hand of the user. Also, for example, for a user inept at fine operations, the terminal device 30 makes it easy to touch the operation buttons by displaying the operation buttons to be large. Also, for example, for a user with a fractured foot, the terminal device 30 may not display an operation button raising/lowering the position of the lower leg section or may make the operation inoperable. Thereby, it is unnecessary for the user to make a conscious effort not to perform the operation of moving the feet. Thus, in the terminal device 30, the operationability of the bed 10 can be improved because the display of the operators can be diversified.

For example, according to the user or according to the bed 10 to be controlled, the terminal device 30 switches between a format (also called a first display format) of simultaneously displaying the display button raising/lowering the position of the lower leg section and another operation button (the back section, the seat section, etc.) and a format (also called a second display format) of displaying only the other display button and not displaying the operation button raising/lowering the position of the lower leg section. Thereby, the terminal device 30 can display the operation buttons suited to each user or each bed; and the operationability of the bed 10 can be improved.

(Operation of Bed 10)

Operations of the bed 10 will now be described.

Figure 2:
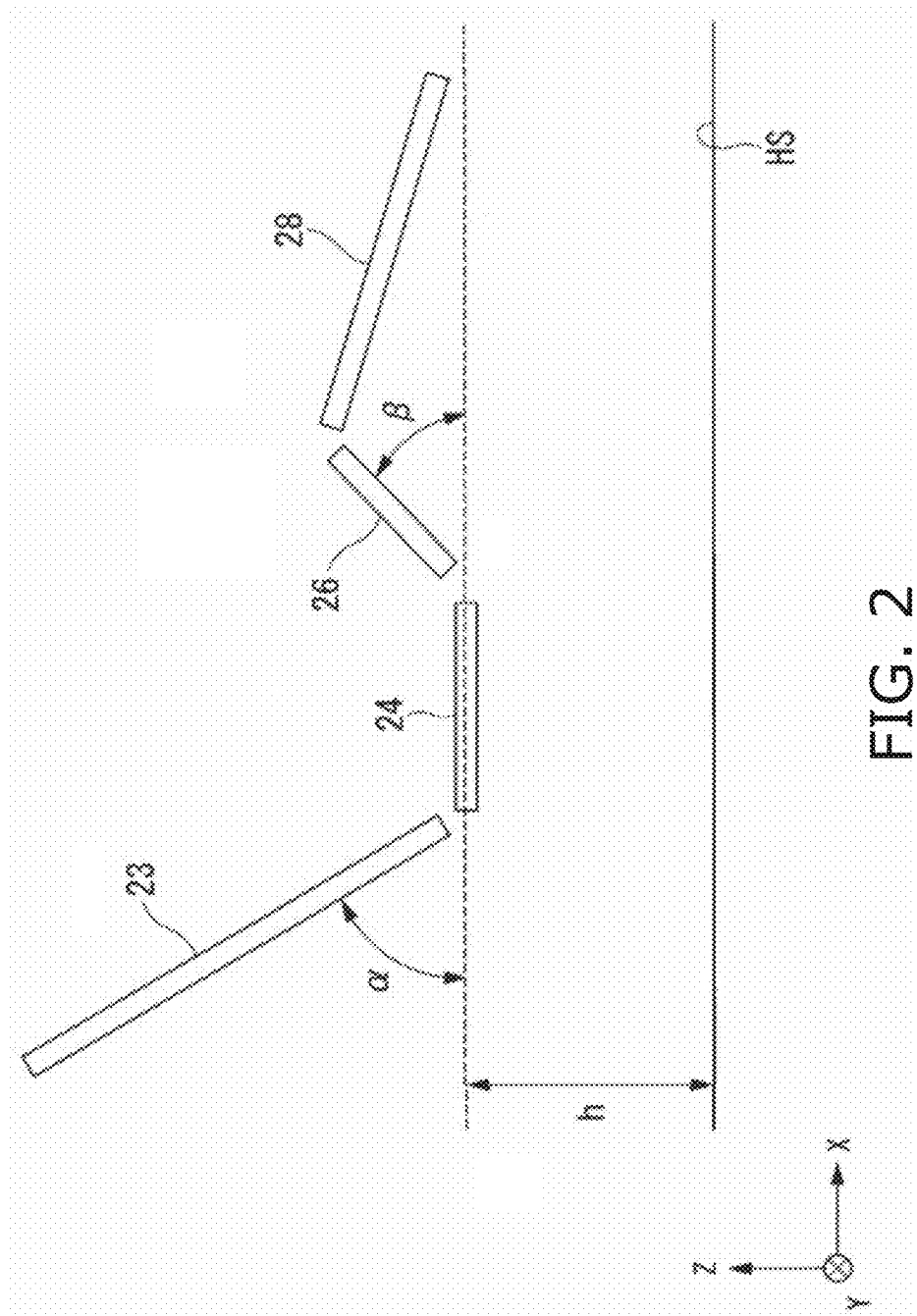
FIG. 2 is a drawing describing operations of the bed according to the same embodiment.

FIG. 2 is a drawing describing the operations of the bed 10.

A back section 23, a seat section 24, an upper leg section 26, and a lower leg section 28 are subdivided and provided in the frame of the bed 10 is order from the head side toward the foot side. The seat section 24 is fixed to the frame. The height of the bed 10 (hereinbelow, called the "bed height") is controllable by the driver. The bed height is, for example, a height h of the bed 10 in a vertical direction (a Z-axis direction of FIG. 2) from the ground surface (a plane HS shown in FIG. 2) to a prescribed member of the bed 10. As an example hereinbelow, the height h to the seat section 24 is described as the bed height. The back section 23 is provided in the frame to be rotatable with the seat section 24 side as the center. The upper leg section 26 is provided in the bed frame to be rotatable with the seat section 24 side as the center. Also, the lower leg section 28 is linked to the upper leg section 26. A raise angle α (hereinbelow, called a "first rotation angle α") of the back section 23 from the horizontal state and a raise angle β (hereinbelow, called the "second rotation angle β") in of the upper leg section 26 from the horizontal state each are controllable by the driver. The driver is described as being able to control the bed height h, the first rotation angle α, and the second rotation angle β as an example hereinbelow; but any member may be rotatable and any member may be extendable/retractable in the bed 10. Normally, a mattress MT is placed on the back section 23, the seat section 24, the upper leg section 26, and the lower leg section 28. The driver is controlled by the control box 22 based on an operation instruction input by the user operating the handy switch 21.

(Configuration of Bed 10)

The configuration of the bed 10 will now be described.

Figure 3:
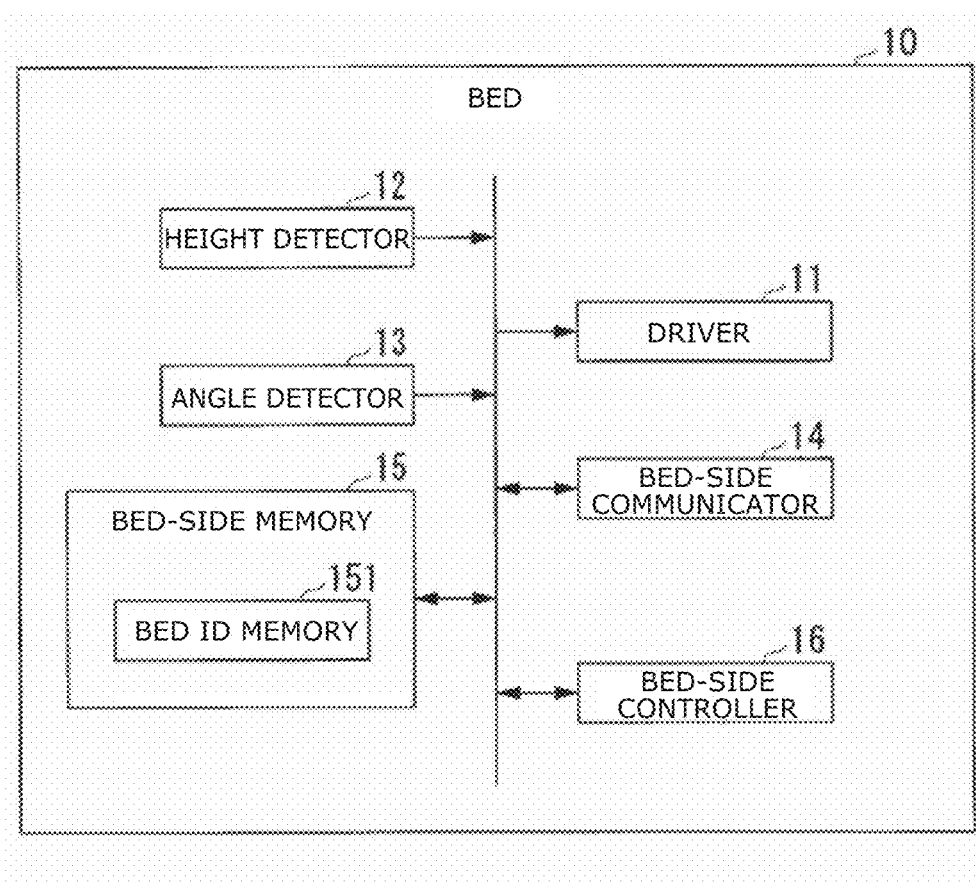
FIG. 3 is a block diagram showing the configuration of the bed according to the same embodiment.

FIG. 3 is a block diagram showing the configuration of the bed 10.

The bed 10 includes a height detector 12, an angle detector 13, a driver 11, a bed-side communicator 14, bed-side memory 15, and a bed-side controller 16.

The driver 11 includes electric actuators and modifies the position and/or the angle of each member of the bed 10.

The height detector 12 includes a sensor and detects the bed height h. For example, the height detector 12 detects the position of a piston rod of an electric actuator that can modify the bed height h. There is a correlation between the bed height h and the position of the piston rod; and data of the correlation is pre-stored in the bed-side memory 15. Then, by referring to the data, the height detector 12 can detect the bed height h based on the position of the piston rod. The height detector 12 notifies the bed-side controller 16 of the detected bed height h.

The angle detector 13 includes a sensor and detects the first rotation angle α and the second rotation angle β. For example, the angle detector 13 detects the positions of the piston rods of electric actuators that can modify the first rotation angle α and the second rotation angle β. There is a correlation between the positions of the piston rods and the first rotation angle α and the second rotation angle β; and data of the correlation is pre-stored in the bed-side memory 15. Then, by referring to the data, the angle detector 13 can detect the first rotation angle α and the second rotation angle β based on the positions of the piston rods. The angle detector 13 notifies the bed-side controller 16 of the detected first rotation angle α and the detected second rotation angle β.

The bed-side communicator 14 includes, for example, a communication IC (Integrated Circuit) and communicates with other devices such as the terminal device 30, etc. The bed-side communicator 14 receives a control command from the terminal device 30. The bed-side communicator 14 outputs the received control command to the bed-side controller 16. Here, the control command is a command instructing the operation content of the driver 11. For example, the operation type (extend, retract, stop, etc.), the operation amount, the operation speed, etc., may be included in the control command. Also, the control command may directly indicate the operation type (extend, retract, stop, etc.), the operation amount, the operation speed, etc., and may be a code pre-associated with these control values. Also, the control command may simultaneously instruct multiple operations or may instruct multiple operations in sequence. In such a case, the multiple operations may be performed by controlling one electric actuator or may be performed by controlling multiple electric actuators in combination. The bed-side communicator 14 is included in the handy switch 21 or the control box 22. However, the bed-side communicator 14 may be included in another location.

The bed-side memory 15 includes, for example, a HDD (Hard Disk Drive), a SSD (Solid State Drive), EEPROM (Electrically Erasable Programmable Read-Only Memory), ROM (Read-Only Memory), RAM (Random Access Memory), etc., and stores programs, various information processed by the bed 10, etc. The bed-side memory 15 is not limited to being built into the bed 10 and may be an externally-attached memory device connected by a digital input/output port such as USB (Universal Serial Bus) (registered trademark), etc. The bed-side memory 15 includes bed ID memory 151.

The bed ID memory 151 stores a bed ID (IDentifier). The bed ID is identification information allotted to the bed 10. The bed ID may be identification information unique to an individual bed 10 or may be identification information common to the same model of bed 10.

The bed-side controller 16 controls each configuration of the bed 10. For example, the bed-side controller 16 may be realized by an arithmetic device (e.g., a CPU (Central Processing Unit)) included in the bed 10 executing a program stored in the bed ID memory 151. Also, for example, the bed-side controller 16 may be realized as an integrated circuit such as an ASIC (Application Specific Integrated Circuit), etc. Via the bed-side communicator 14, the bed-side controller 16 notifies the terminal device 30 of the current state of the bed height h, the first rotation angle α, the second rotation angle β, etc. Also, according to the control command received from the terminal device 30, the bed-side controller 16 operates and stops the driver 11.

A communication connection is established between the bed 10 and the terminal device 30 when the driver 11 is controlled according to the control command from the terminal device 30. The establishment of the communication connection is a process of mutual authentication by the communication parties and is, for example, pairing by Bluetooth (registered trademark) communication. Also, the communication connection between the bed 10 and the terminal device 30 may be established by wireless communication such as Wi-H (registered trademark), LTE (Long Term Evolution), etc., and/or wired communication via various connection cables. The bed-side controller 16 uses only the terminal device 30 having the established communication connection as its own control terminal. That is, the bed-side controller 16 accepts control commands transmitted from the terminal device 30 having the established communication connection, but does not accept control commands transmitted from other terminal devices 30.

As an example in the embodiment, the combination of the terminal device 30 and the bed 10 to have the communication connection established is selected by the terminal device 30. In the establishment of the communication connection, the bed-side controller 16 transmits, to the terminal device 30, its own bed ID stored in the bed ID memory 151. When the terminal device 30 receives the bed ID, the terminal device 30 transmits the terminal ID for establishing the communication connection to the bed 10 indicated by the bed ID. The terminal ID is information that uniquely identifies the terminal device 30. The terminal ID may be information identifying the terminal user of the terminal device 30. Then, when the bed-side controller 16 receives the terminal ID, the bed-side controller 16 authenticates the terminal device 30 indicated by the terminal ID as the party for establishing the communication connection. Thereafter, the bed-side controller 16 accepts only control commands from the authenticated terminal device 30. Thereby, in the bed system 1, the safety of the bed 10 can be improved because only the designated terminal device 30 can operate the bed 10.

(Configuration of Terminal Device 30)

The configuration of the terminal device 30 will now be described.

Figure 4:
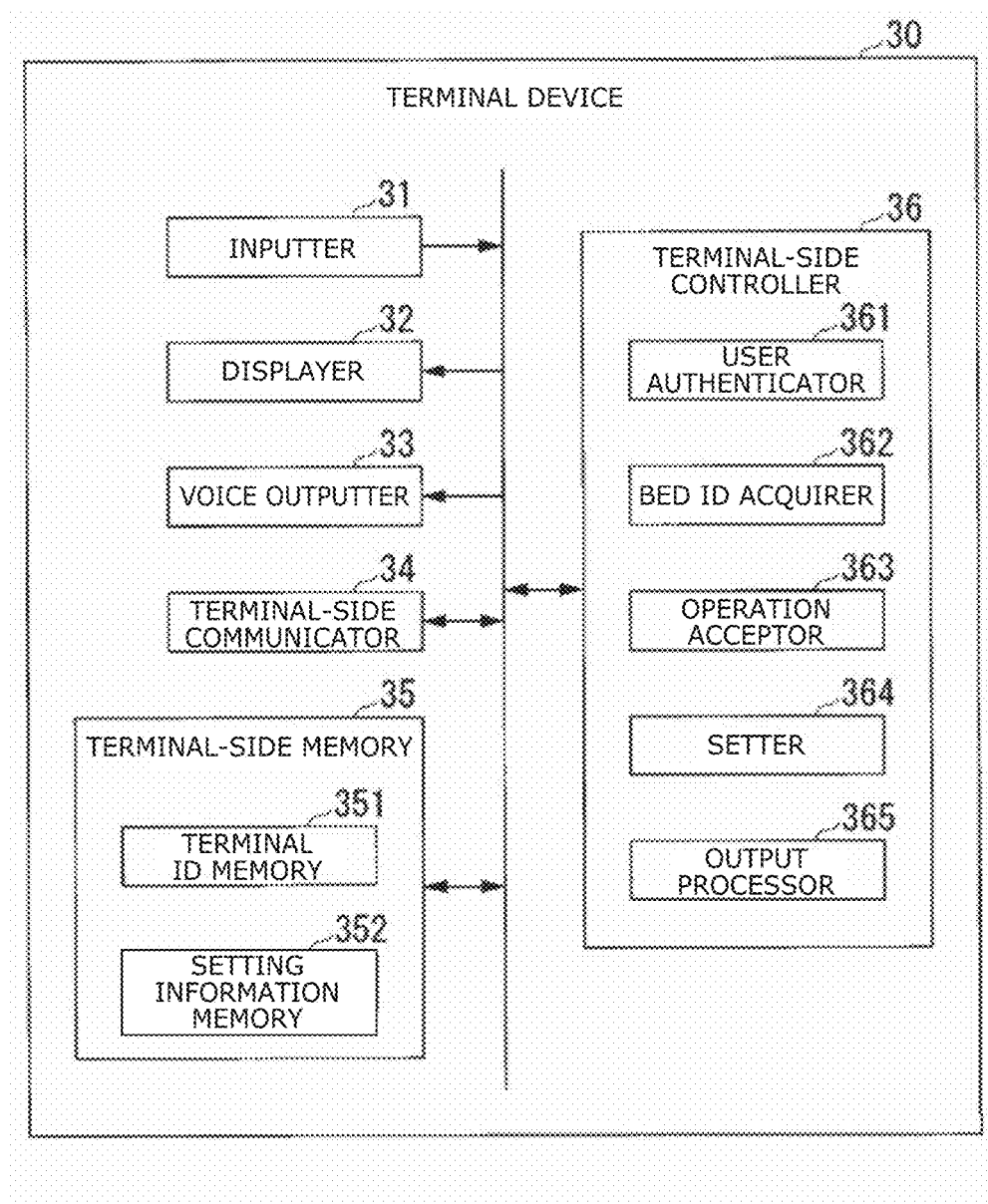
FIG. 4 is a block diagram showing the configuration of the terminal device according to the same embodiment.

FIG. 4 is a block diagram showing the configuration of the terminal device 30.

The terminal device 30 includes an inputter 31, a displayer 32, a voice outputter 33, a terminal-side communicator 34, terminal-side memory 35, and a terminal-side controller 36.

The inputter 31 includes, for example, a touch sensor of a touch panel and accepts an operation input from the user.

The displayer 32 includes, for example, the liquid crystal display panel of a touch panel, an organic EL (ElectroLuminescence) display panel, etc., displays the state of the bed 10, and displays the operation buttons for controlling the operations of the bed 10.

The voice outputter 33 includes, for example, a speaker, etc., and outputs a voice and/or a warning sound for operation guidance.

The terminal-side communicator 34 includes, for example, a communication IC and communicates with the other devices of the bed 10, etc.

The terminal-side memory 35 includes, for example, a HDD, a SSD, ROM, RAM, etc., and stores programs, various information processed by the terminal device 30, etc. The terminal-side memory 35 is not limited to being built into the terminal device 30 and may be an externally-attached memory device. The terminal-side memory 35 includes a terminal ID memory 351 and a setting information memory 352.

The terminal ID memory 351 stores the terminal ID. The terminal ID may be, for example, a MAC address, an IP address, etc.

The setting information memory 352 stores setting information. The operation button setting information may be stored for each terminal ID, for each user ID, and for each bed ID. That is, the setting information may be information indicating the display setting of the operation buttons for each terminal device 30, for each bed user, for each terminal user, and for each bed 10. Also, multiple setting information may be stored for each terminal device 30, for each bed user, for each terminal user, and for each bed 10. In such a case, a priority order may be set for each setting information. Also, the setting information may be associated explicitly or implicitly with the terminal ID, the user ID, the bed ID, etc. An explicit association refers to being associated with each other in the data. An implicit association refers to not having a distinct association in the data but having a prescribed relationship by being managed in the terminal device 30, etc. As an example hereinbelow, a case will be described where the setting information is stored for each user ID.

Here, in the embodiment, the two types of setting information of the operation setting information and the display setting information exist. The operation setting information is information indicating the correspondence between the operation buttons and the operations of the bed 10. The data configuration of the operation setting information is described below. By referring to the operation setting information, the terminal device 30 can identify the operation desired by the terminal user and the control command for performing the operation. Also, by referring to the operation setting information, the terminal device 30 can control the activation and the deactivation of the operation buttons. For example, the terminal device 30 accepts the operation of an operation button only in the case where the operation corresponding to the operation button is authorized in the operation setting information. The terminal device 30 may differentiate a deactivated operation button from an activated operation button by non-display, reducing the brightness, etc. The format in which both the deactivated operation button and the activated operation button are displayed without differentiating also is called the first display format; and the format in which only the activated operation button is displayed also is called the second display format. The first display format and the second format may be switched by the terminal-side controller 36.

The display setting information is information indicating the display mode of the operation buttons in the control screen. The data configuration of the display setting information is described below. By referring to the display setting information, the terminal device 30 can cause the display mode of the operation buttons in the control screen to be different for each terminal user. The shape, the pattern, the color, and the arrangement of each operation button may be settable individually by the terminal user. The display format in which the operation buttons to be displayed are caused to be different for each user also is called the first display format; and the display format in which the same operation buttons are displayed for all of the users also is called the first display format. The first display format and the second format may be switched by the terminal-side controller 36.

The terminal-side controller 36 controls each configuration of the terminal device 30. For example, the terminal-side controller 36 may be realized by an arithmetic device (e.g., a CPU) included in the terminal device 30 executing a program stored in the terminal-side memory 35. Also, for example, the terminal-side controller 36 may be realized as an integrated circuit such as an ASIC, etc. The terminal-side controller 36 includes a user authenticator 361, a bed ID acquirer 362, an operation acceptor 363, a setter 364, and an output processor 365.

The user authenticator 361 authenticates the user. For example, the user authenticator 361 may authenticate the user based on a user ID, a password, etc., input via the inputter 31. Also, the user authenticator 361 may perform biometric authentication such as fingerprint authentication, etc., or may perform the authentication using a unique IC card of the user. The user authenticator 361 notifies the output processor 365 of the authentication result.

The bed ID acquirer 362 acquires the bed ID from the bed 10 via the terminal-side communicator 34. The bed 10 notifies the output processor 365 of the acquired bed ID.

The operation acceptor 363 accepts an operation by the terminal user via the inputter 31. Operations accepted by the operation acceptor 363 include, for example, a bed selection operation, a setting operation, and a control operation. The bed selection operation is an operation of selecting the bed 10 to have the communication connection established. The setting operation is an operation of inputting the setting values described in the setting information. The control operation is an operation of designating the control command to be transmitted to the bed 10. The operation acceptor 363 notifies the output processor 365 of the content of the accepted operation.

The setter 364 edits the setting information. Here, editing includes newly generating information, updating the content of the information, and erasing the information. The setter 364 stores the setting information after the editing in the setting information memory 352.

The output processor 365 causes the displayer 32 to display the various screens. For example, the output processor 365 displays a bed selection screen, a setting screen, a control screen, etc., in the displayer 32. In the display of the control screen, the output processor 365 refers to the setting information and determines the display modes of the operation buttons and/or the types of the operation buttons disposed in the control screen. Thereby, the display modes of the operation buttons and/or the types of the operation buttons displayed are switched for each terminal device 30, for each bed user, for each terminal user, for each bed 10, or for each combination thereof.

Also, the output processor 365 performs processing based on the operation content accepted by the operation acceptor 363. For example, in the case where the operation is the bed selection operation, the output processor 365 transmits the terminal ID to the selected bed 10. For example, in the case where the operation is the setting operation, the output processor 365 stores the setting information of the input setting values in the setting information memory 352. For example, in the case where the operation is the control operation, the output processor 365 transmits the designated control command to the bed 10.

(Data Configuration of Setting Information)

First, the data configuration of the operation setting information will be described.

FIG. 5 is a figure showing the data configuration of the setting information.

In the example shown in FIG. 5, the operation setting information is information that mutually associates the user ID, head speed information, height speed information, combination enablement information, head operation enablement information, foot operation enablement information, height operation enablement information, memory enablement information, head memory information, foot memory information, height memory information, and bed-exit notification enablement information.

The head speed information indicates the rotation speed of modifying the first rotation angle $\alpha$. The height speed information indicates the raising/lowering speed of modifying the bed height h. The combination enablement information indicates the enablement of the operations of the multiple electric actuators in combination. The head operation enablement information indicates the enablement of the rotation operation of modifying the first rotation angle $\alpha$. The foot operation enablement information indicates the enablement of the rotation operation of modifying the second rotation angle $\beta$. The height operation enablement information indicates the enablement of the lifting/lowering operation of modifying the bed height h. The memory enablement information indicates the enablement of an operation (hereinbelow, called the "memory operation") of modifying the state of the bed 10 to predetermined target values of the bed height h, the first rotation angle $\alpha$, and the second rotation angle $\beta$. The head memory information indicates the target value of the first rotation angle $\alpha$ in the memory operation. The foot memory information indicates the target value of the second rotation angle $\beta$ in the memory operation. The height memory information indicates the target value of the bed height h in the memory operation. The bed-exit notification enablement information indicates whether or not to notify when the bed user exits from the bed 10.

The data configuration of the display setting information will now be described.

FIG. 6 is a figure showing the data configuration of the display setting information.

In the example shown in FIG. 6, the display setting information is information in which the user ID and display pattern information are associated with each other.

The display pattern information indicates the display pattern of the control screen. Multiple display patterns are prepared in the embodiment. Then, in each display pattern, the display modes of the operation buttons are different, and/or the types of the operation buttons to be displayed are different.

(Operations of Bed System 1)

Operations of the bed system 1 will now be described.

Figure 7:
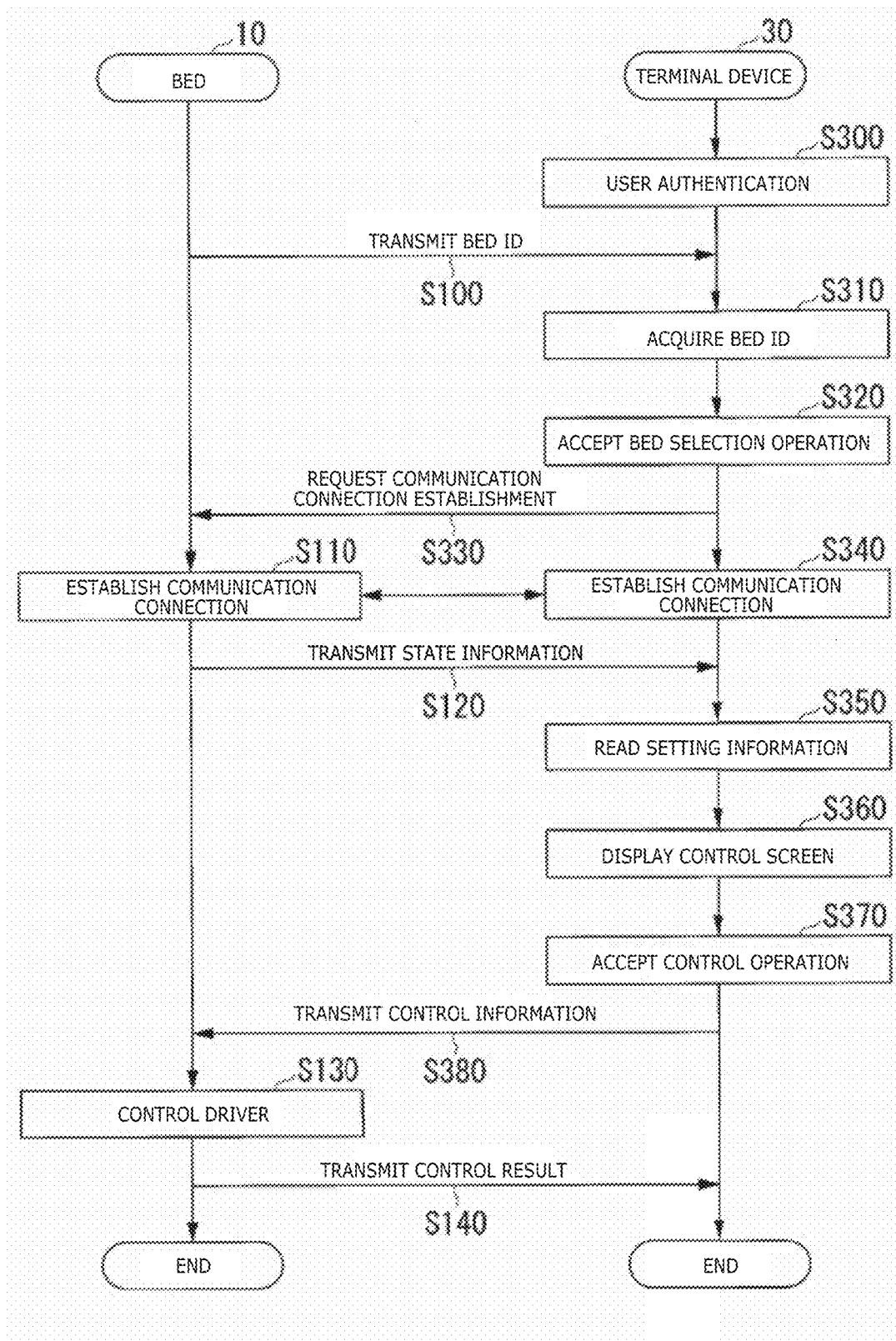
FIG. 7 is a sequence chart showing the operations of the bed system according to the same embodiment.

FIG. 7 is a sequence chart showing the flow of the processing by the bed system 1.

(Step S300)

The terminal device 30 performs a user authentication. Subsequently, the processing of the bed system 1 proceeds to step S100.

(Step S100)

The bed 10 transmits the bed ID to the terminal device 30. Subsequently, the processing of the bed system 1 proceeds to step S310.

(Step S310)

The terminal device 30 acquires the bed ID from the bed 10 and displays the bed selection screen. Specific examples of the bed selection screen are described below. By acquiring the bed ID, the terminal device 30 can identify the model of the bed 10, the control commands acceptable by the bed 10, etc. Subsequently, the processing of the bed system 1 proceeds to step S320.

(Step S320)

The terminal device 30 accepts the bed selection operation from the terminal user. Subsequently, the processing of the bed system 1 proceeds to step S330.

(Step S330)

The terminal device 30 requests the establishment of the communication connection for the bed 10 designated by the bed selection operation. Subsequently, the processing of the bed system 1 proceeds to steps S110 and S340.

(Steps S110 and S340)

The communication connection between the bed 10 and the terminal device 30 is established. Thereby, the bed 10 performs the operations according to the control command transmitted from the terminal device 30. In other words, the bed 10 is controllable by operating the terminal device 30. Subsequently, the processing of the bed system 1 proceeds to step S120.

(Step S120)

The bed 10 transmits, to the terminal device 30, state information indicating its own state such as the bed height h, the first rotation angle $\alpha$, the second rotation angle $\beta$, etc. Subsequently, the processing of the bed system 1 proceeds to step S350.

(Step S350)

The terminal device 30 reads the setting information from the setting information memory 352. Although the processing is not illustrated herein, the setting information can be edited by a setting operation via a setting screen. Specific examples of the setting screen are described below. Subsequently, the processing of the bed system 1 proceeds to step S360.

(Step S360)

The terminal device 30 displays a control screen based on the setting information. Specific examples of the control screen are described below. Subsequently, the processing of the bed system 1 proceeds to step S370.

(Step S370)

The terminal device 30 accepts a control operation. Subsequently, the processing of the bed system 1 proceeds to step S380.

(Step S380)

The terminal device 30 designates the control command corresponding to the control operation. The terminal device 30 transmits the control information indicating the control command to the bed 10. Here, even in the case where the same operation is performed, there are cases where different control commands are allotted to each model of the bed 10. In such a case, if uniform control commands are transmitted regardless of the model of the bed 10, there is a possibility that the bed 10 may undesirably misoperate. Therefore, the terminal device 30 pre-stores the data indicating the correspondence between the operation and the control command beforehand for each model of the bed 10. Then, from the data, the terminal device 30 designates the control command corresponding to the control operation by referring to the part of the bed 10 to be controlled. Thereby, the terminal device 30 can appropriately control diverse models of beds 10. Subsequently, the processing of the bed system 1 proceeds to step S130.

(Step S130)

The bed 10 operates the driver 11 according to the control command indicated by the control information. Subsequently, the processing of the bed system 1 proceeds to step S140.

(Step S140)

The bed 10 transmits, to the terminal device 30, information indicating the control result of the driver 11. For example, the values of the bed height h, the first rotation angle α, and the second rotation angle β, etc., may be included in the control result. According to the reception of the control result, the terminal device 30 can accept the next control operation. Subsequently, in the case where the control operation is performed, the processing of the bed system 1 proceeds to step S370; and in the case where the operation of the bed 10 is unnecessary, the processing shown in FIG. 7 ends.

As appropriate, any processing shown in FIG. 7 may be partially omitted and the sequence may be interchanged when executed. For example, the processing of step S300 may be omitted or may be executed after the processing of steps S110 and S340, etc.

(Screen Examples)

Screen examples that are displayed by the terminal device 30 will now be described.

First, an example of the bed selection screen will be described.

Figure 8:
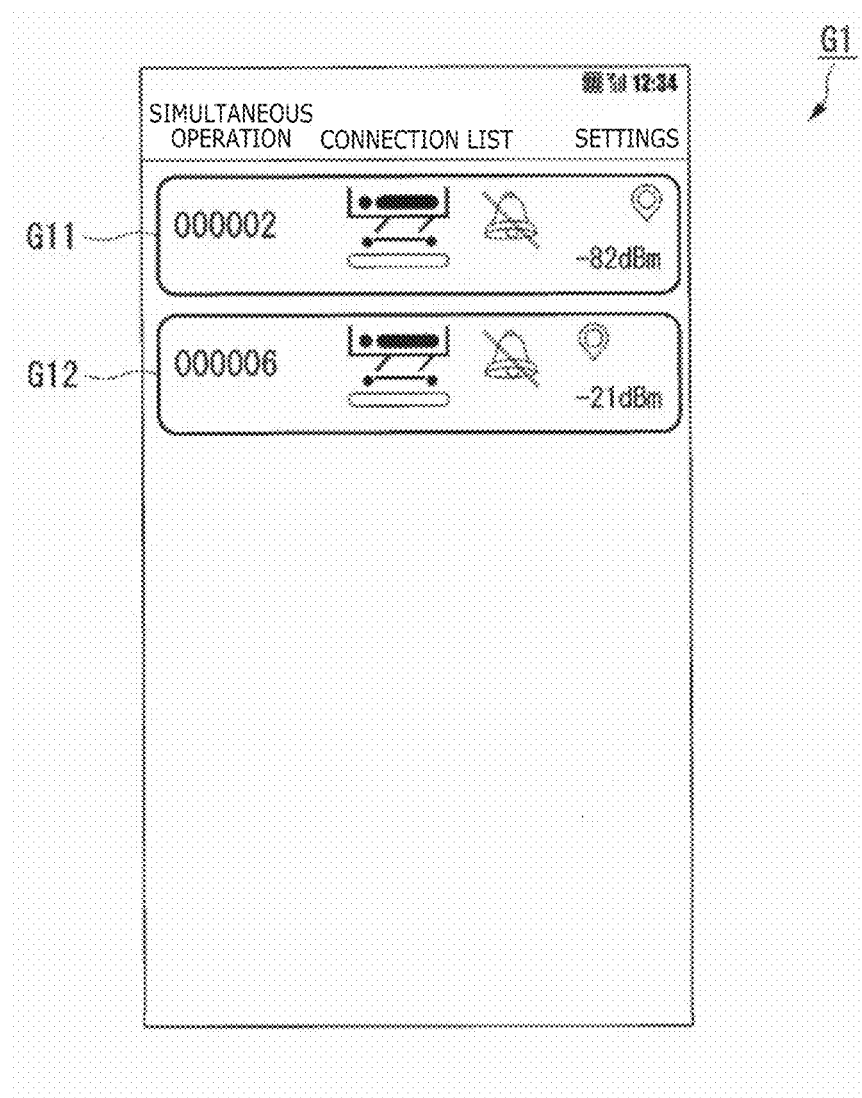
FIG. 8 is a drawing showing the bed selection screen according to the same embodiment.

FIG. 8 is a drawing showing the bed selection screen.

In a bed selection screen G1 shown in FIG. 8, selection buttons G11 and G12 are provided as operators for selecting one of two beds 10 of which the terminal device 30 has acquired the bed IDs. The selection buttons G11 and G12 each may display information such as the bed ID, the communication radio wave intensity for each bed 10, etc.

An example of the setting screen will now be described.

Figure 9:
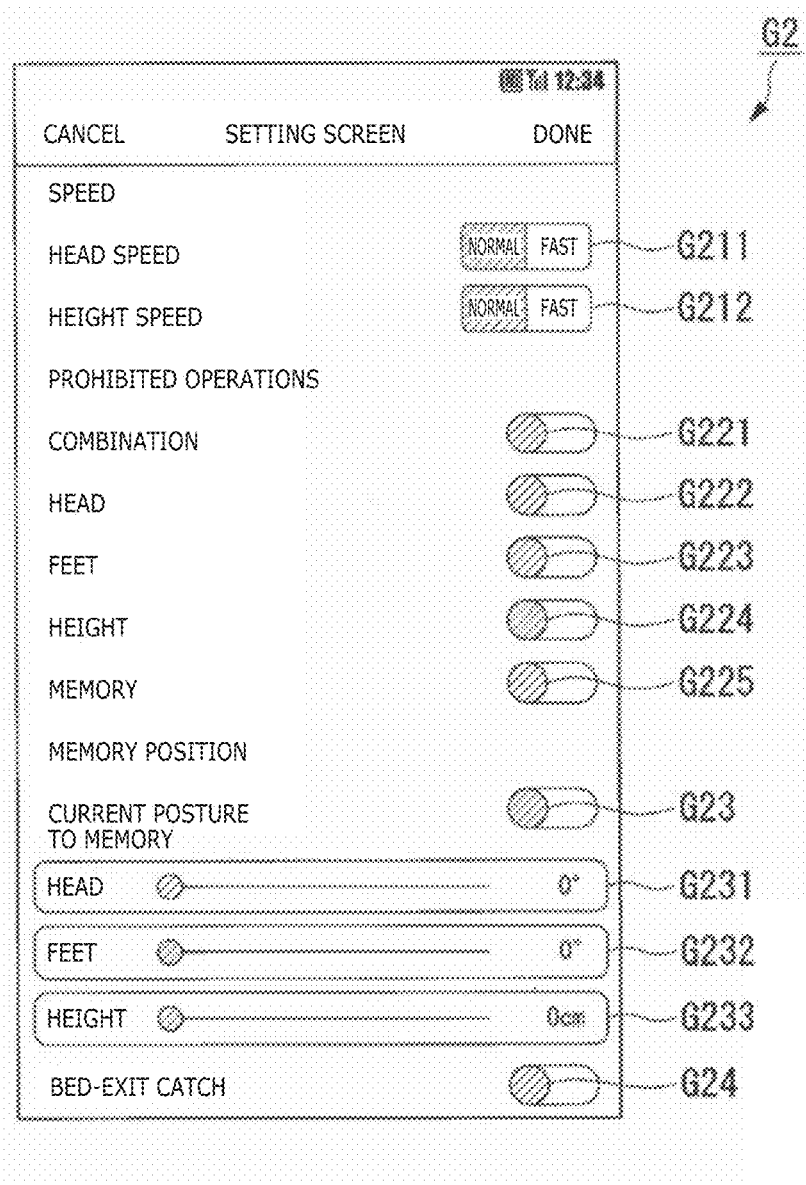
FIG. 9 is a drawing showing the setting screen according to the same embodiment.

FIG. 9 is a drawing showing the setting screen.

Setting buttons G211, G212, G221 to G225, G23, G231 to G233, and G24 are provided in a setting screen G2 shown in FIG. 9 as operators for designating the setting value of each item of the setting information. The setting button G211 is an operator for setting the head speed information. The setting button G212 is an operator for setting the height speed information. The setting button G221 is an operator for setting the combination enablement information. The setting button G222 is an operator for setting the head operation enablement information. The setting button G223 is an operator for setting the foot operation enablement information. The setting button G224 is an operator for setting the height operation enablement information. The setting button G225 is an operator for setting the memory enablement information. The setting button G23 is an operator for setting the current first rotation angle α, second rotation angle β, and bed height h of the bed 10 in the head memory information, the foot memory information, and the height memory information. The setting button G231 is an operator for adjusting the setting value of the head memory information. The setting button G232 is an operator for adjusting the setting value of the foot memory information. The setting button G233 is an operator for adjusting the setting value of the height memory information. The setting button G24 is an operator for setting the bed-exit notification enablement information. A display mode of the operators other than that shown in FIG. 9 also may be settable in the setting screen.

Control screens will now be described.

Figure 10:
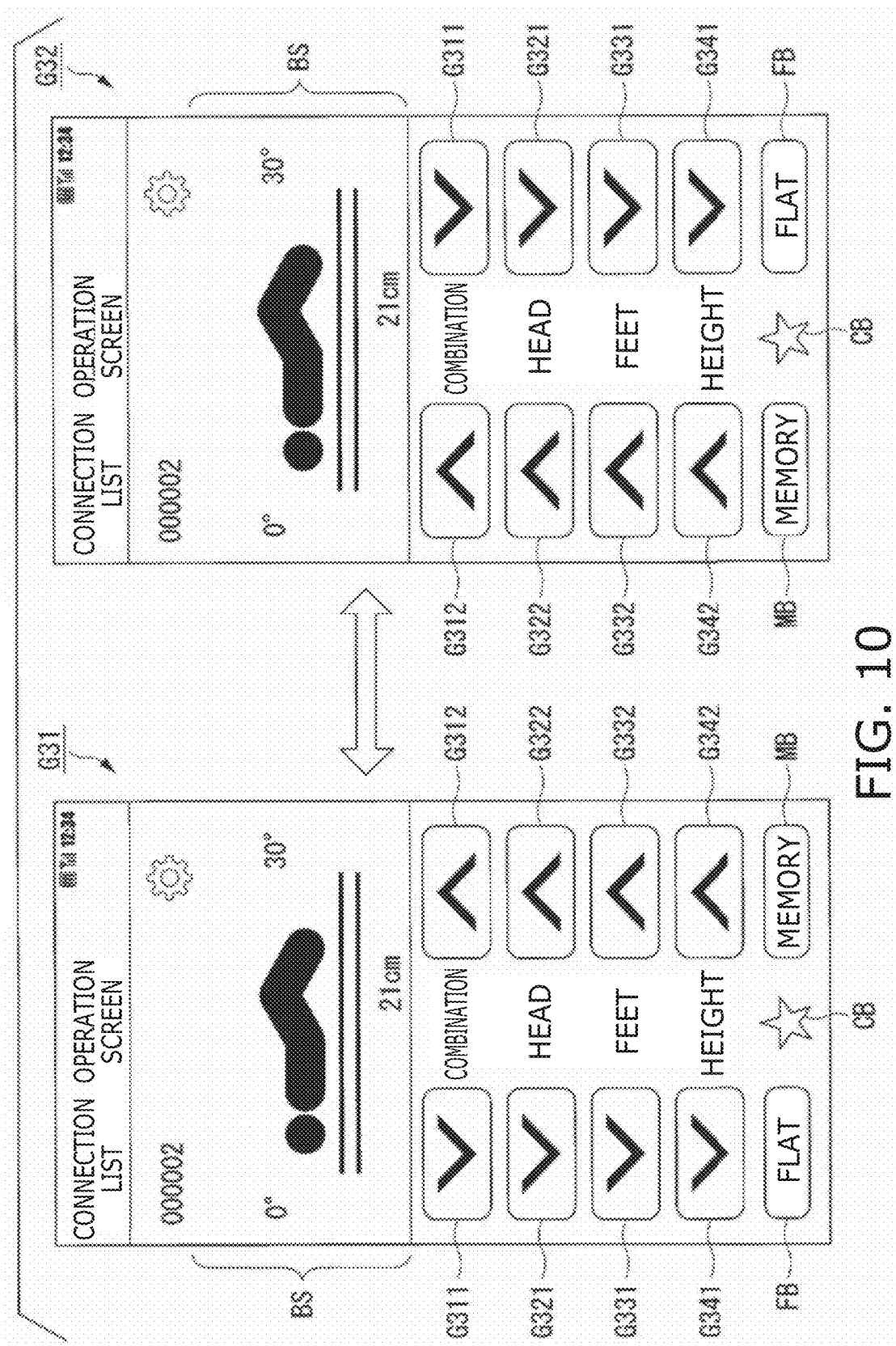
FIG. 10 is a first drawing showing a control screen according to the same embodiment.
Figure 11:
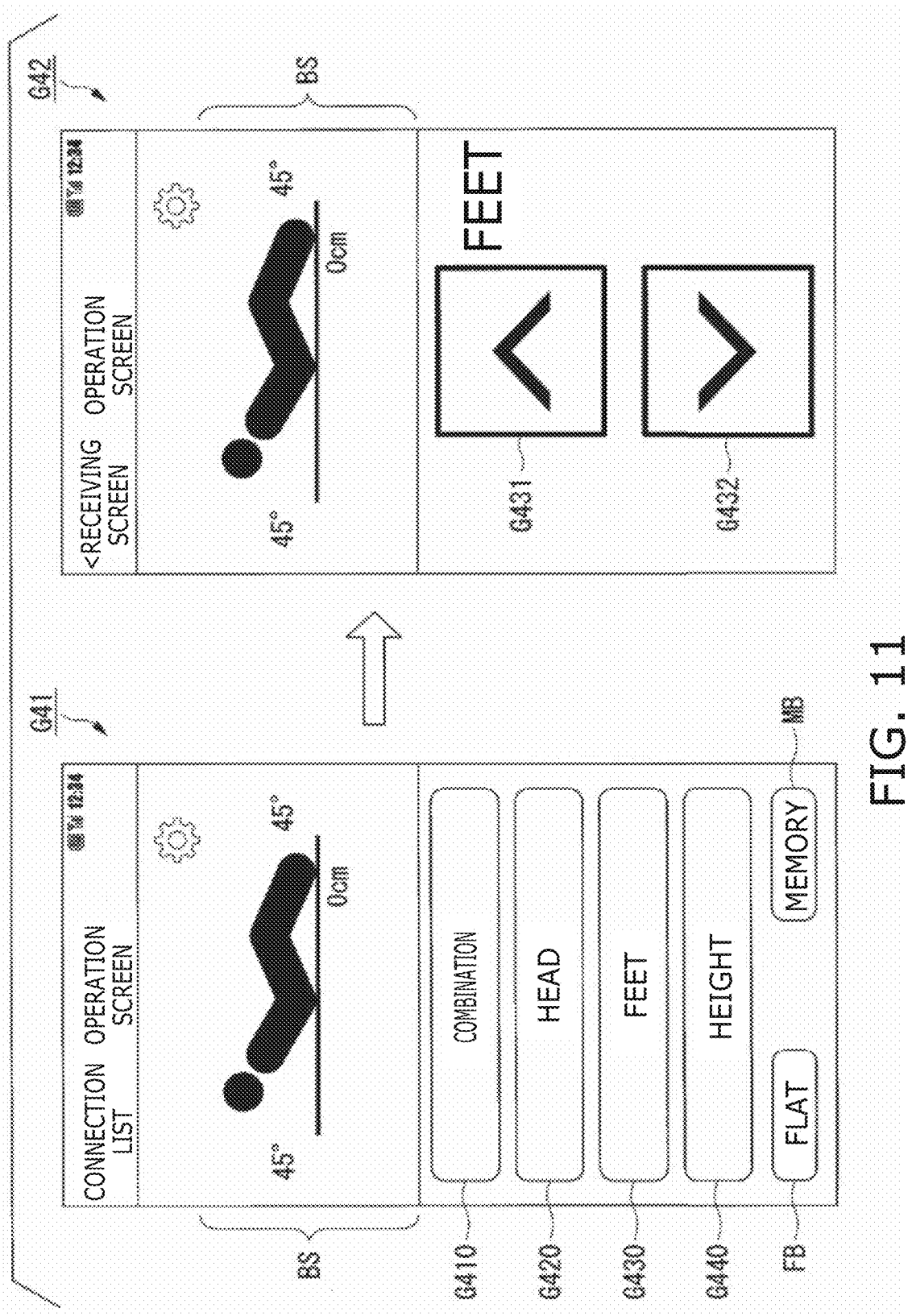
FIG. 11 is a second drawing showing a control screen according to the same embodiment.
Figure 12:
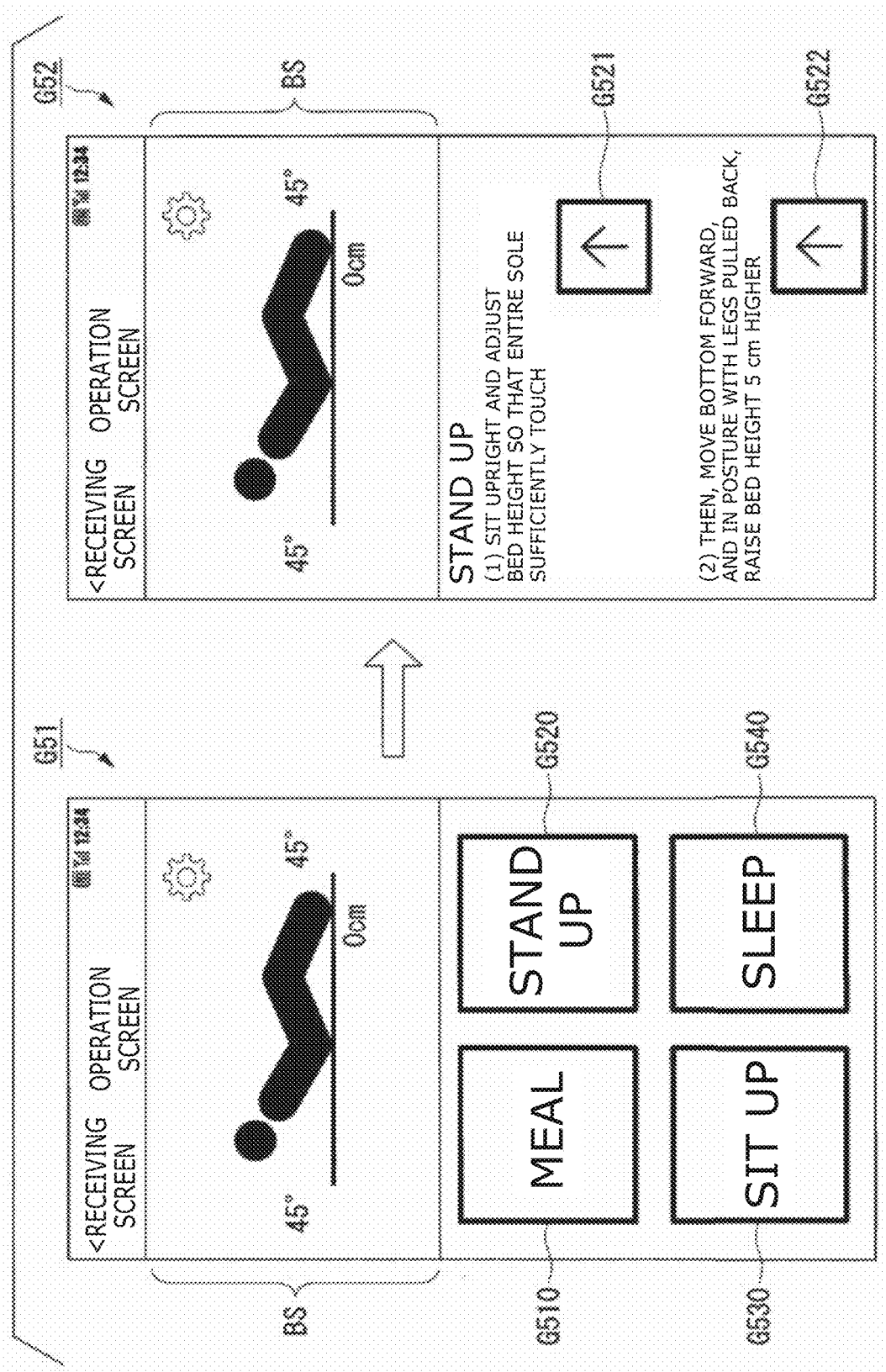
FIG. 12 is a third drawing showing a control screen according to the same embodiment.

FIG. 10 to FIG. 12 are drawings showing control screens.

A bed state display field BS that indicates the state of the bed 10 (the first rotation angle α, the second rotation angle β, the bed height h, etc.) is provided in a control screen G31 shown in FIG. 10. Also, operation buttons G311, G312, G321, G322, G331, G332, G341, G342, FB, and MB are provided in the control screen G31 as operators for designating control commands. The operation buttons G311 and G312 are operators corresponding to the operation of modifying both the first rotation angle α and the second rotation angle β. The operation buttons G321 and G322 are operators corresponding to the operation of modifying the first rotation angle α. The operation buttons G331 and G332 are operators corresponding to the operation of modifying the second rotation angle β. The operation buttons G341 and G342 are operators corresponding to the operation of modifying the bed height h. Also, the operation buttons G311, G321, G331, and G341 correspond to operations of reducing the first rotation angle α, the second rotation angle β, the bed height h, and both the first rotation angle α and the second rotation angle β. Also, the operation buttons G312, G322, G332, and G342 correspond to operations of increasing the bed height h, the second rotation angle β, the first rotation angle α, and both the first rotation angle α and the second rotation angle β. The operation button FB is an operator corresponding to an operation of setting both the first rotation angle α and the second rotation angle β to zero and setting each section to the horizontal state. The operation button MB is an operator corresponding to a memory operation.

Here, a pattern switching button CB is disposed in the control screen G31. The pattern switching button CB is an operator for switching the display pattern of the control screen. That is, the pattern switching button CB is an example of an operator for accepting a display mode modification instruction of modifying the display mode of the operation buttons. When the pattern switching button CB is operated in the control screen G31, the terminal device 30 switches the display to a control screen G32. Also, when the pattern switching button CB is operated in the control screen G32, the terminal device 30 switches the display to the control screen G31. Operation buttons similar to those of the control screen G31 are disposed in the control screen G32. However, the arrangement of the operation buttons is modified to reverse left and right. Thereby, for example, even for a terminal user of which one hand is handicapped, the desired operation buttons can be moved to a range reached by the thumb of the usable hand. Thereby, the bed system 1 can improve the operationability of the bed 10.

The display patterns of the control screen are not limited to two; and three or more may be prepared. Also, other than the arrangement of the operation buttons, the size, the shape, the pattern, and the color also may be different between the display patterns. Also, the size, the shape, the pattern, and the color may be different for the individual operation buttons between the display patterns. Also, the size, the shape, the pattern, the color, the arrangement, etc., of the operation buttons may be modifiable individually. Also, the method for operating the individual operation buttons may be different. For example, an operation button that accepts the operation in the case of a long-press or an operation button that accepts the operation in the case of a double-tap may be provided. Thus, by accepting only the designated operation method, an undesirable operation of the bed 10 according to a misoperation of an operation button can be prevented.

Operation buttons G410, G420, G430, and G440 are provided in a control screen G41 shown in FIG. 11. The operation buttons G410, G420, G430, and G440 are operators for selecting the electric actuators of the control object. The operation button G410 is an operator corresponding to the operation of modifying both the first rotation angle α and the second rotation angle β. The operation button G420 is an operator corresponding to the operation of modifying the first rotation angle α. The operation button G430 is an operator corresponding to the operation of modifying the second rotation angle β. The operation button G440 is an operator corresponding to the operation of modifying the bed height h. The operations may be called the first operation, the second operation, . . . .

When the control object is selected, the terminal device 30 causes the display to transition to a control screen for accepting an input of the operation amount and the operation direction. For example, when the operation button G430 is operated, the terminal device 30 displays a control screen G42. Operation buttons G431 and G432 are provided in the control screen G42. The operation button G431 corresponds to the operation of increasing the second rotation angle β. The operation button G432 corresponds to the operation of reducing the second rotation angle β. Thus, in the example shown in FIG. 11, the terminal device 30 requests the operation of multiple operation buttons in order to cause the bed 10 to perform one operation. Therefore, even when one operation button is operated erroneously, the bed 10 does not operate immediately. Thereby, the bed system 1 can improve the safety of the bed 10.

The terminal device 30 may request multiple operation buttons to be operated simultaneously to cause the bed 10 to perform one operation. In such a case, for example, the bed 10 does not operate if the two operation buttons are not touched simultaneously. Therefore, even when one operation button is operated erroneously, the bed 10 does not operate immediately. Thereby, the bed system 1 can improve the safety of the bed 10.

The operation buttons that accept the input of the operation amount and the operation direction corresponding respectively to the operation buttons G410, G420, G430, and G440 may be displayed in the control screen G41. That is, the operation buttons G431 and G432 of the display screen G42 may be displayed as being associated with the operation buttons G410, G420, G430, and G440. Thereby, the terminal device 30 can accept the input of the operation amount and the operation direction of the control object from the user in the control screen G41. Here, the display format of the control screen G41 also is called the first display format; and the display format of the control screen G42 also is called the second display format. The first display format is, for example, a format of simultaneously displaying the operation button G420 for controlling the position of the feet and a control button (G410, G420, or the like) for controlling another operation. The second display format is, for example, a format in which only the operation button G430 for controlling the position of the feet is displayed, and an operation button (G410, G420, or the like) for controlling another operation is not displayed. The first display format and the second format may be switched by the terminal-side controller 36.

Operation buttons G510, G520, G530, and G540 are provided in a control screen G51 shown in FIG. 12. The operation buttons G510, G520, G530, and G540 are operators for selecting actions of the bed user. The operation button G510 is an operator for causing the bed 10 to operate to be in a state suited to the bed user having a meal. The operation button G520 is an operator for causing the bed 10 to operate to be in a state suited to the bed user standing up from the bed 10. The operation button G530 is an operator for causing the bed 10 to operate to be in a state suited to the bed user sitting up in the bed. The operation button G540 is an operator for causing the bed 10 to operate to be in a state suited to the bed user sleeping.

When the action of the bed user is selected, the terminal device 30 displays the operation procedure of the bed user and the operation procedure of the bed 10 for performing the selected action. For example, when the operation button G520 is operated, the terminal device 30 displays a control screen G53. Operation buttons G521 and G522 are provided in the control screen G53. The operation buttons G521 and G522 are operators for causing the bed 10 to perform an operation corresponding to each procedure of the action. The bed user can cause the bed 10 to operate to be in a state suited to performing each procedure by operating operation buttons arranged with the description of each procedure. Thereby, the bed user can easily understand the optimal way to move his or her own body and the optimal way to operate the bed 10 to perform the desired action. Therefore, the bed user can utilize the bed 10 appropriately even without knowing the appropriate utilization method of the bed 10. Thereby, the bed system 1 can improve the operationability of the bed 10.

In the example shown in the control screen G52, one operation button G521 or operation button G522 is displayed to be arranged with each operation procedure of the bed user; but one operation button may be displayed as being associated with multiple operation procedures. In such a case, the control command that corresponds to the operation button may be switched sequentially. For example, the operation button may function as the operation button G521 when initially operated, and may function as the operation button G522 when operated next. Thus, the terminal device 30 may modify the control command corresponding to one operation button according to the operation count and/or the operation timing. Thereby, the terminal user can cause the bed 10 to perform different operations by operating the same operation button. The terminal device 30 may dynamically move the operation button to the vicinity of the corresponding operation procedure, or may modify the display and may be able to identify to which operation procedure the operation button corresponds.

The operation buttons that accept the input of the operation amount and the operation direction may be displayed to correspond respectively to the operation buttons G510, G520, G530, and G540 in the control screen G51. That is, the operation buttons G521 and G522 of the display screen G52 may be displayed to be associated with the operation buttons G510, G520, G530, and G540. Thereby, the terminal device 30 can accept the input of the operation amount and the operation direction of the control object from the user in the control screen G51. Here, the display format of the control screen G51 also is called the first display format; and the display format of the control screen G52 also is called the second display format. The first display format is, for example, a format of simultaneously displaying the operation button G520 for causing the bed 10 to operate to be in a state suited to the bed user standing up from the bed 10 and an operation button (G510, G530, etc.) for causing the bed 10 to operate to be in a state suited to another operation. The second display format is, for example, a format in which only the operation button G520 is displayed and another operation button (G510, G530, or the like) is not displayed. The first display format and the second format may be switched by the terminal-side controller 36.

Summary of First Embodiment

As described above, the bed system 1 (an example of the information processing system) includes the bed 10 (an example of the body support apparatus) and the terminal device 30 (an example of the terminal device). The terminal device 30 includes the displayer 32 that displays the operation buttons (the operators) controlling the various operations (the first operation and the second operation) of the bed 10, and the terminal-side controller 36 (the controller) that switches, based on an instruction from an outside, between the first display format of displaying the first operator controlling the first operation and the second operator controlling the second operation in the displayer 32 and the second display format of displaying one of the first operator or the second operator in the displayer 32.

Thereby, the bed system 1 can improve the operationability of the bed 10 by switching the display format according to the user and/or the bed 10 and performing a display suited to the user and/or the bed 10. For example, the operationability of the bed 10 can be improved by not displaying operation buttons that are not operated for each user and/or not displaying operation buttons of operations not corresponding to the bed 10 for each bed 10.

Also, the terminal device 30 includes the operation acceptor 363 (an example of the selection acceptor) and the output processor 365 (an example of the control command transmitter and the display processor). The operation acceptor 363 accepts the selection of the bed 10. The output processor 365 displays the operation button (an example of the operator) corresponding to the selected bed 10 in the displayer 32. The operation acceptor 363 accepts the input of the control command for the bed 10 based on the operation of the operation button. The output processor 365 transmits the input control command to the selected bed 10 according to the operation of the operation button.

Thereby, the bed system 1 displays the selection of the bed 10 and/or the operation buttons based on the setting information corresponding to the bed 10. Therefore, the bed system 1 can customize the display of the operation buttons for each bed 10 to be controlled. That is, the bed system 1 can customize the display of the operation buttons for each bed user. Thereby, the bed system 1 can improve the operationability of the bed 10.

Also, the terminal device 30 further includes the bed ID acquirer 362 (an example of the identification information acquirer). The bed ID acquirer 362 acquires the bed ID (an example of the identification information) associated with the bed 10. The operation acceptor 363 accepts the selection of the bed ID. The output processor 365 displays the operation buttons in the displayer 32 based on the bed ID (based on the selection of the bed ID or based on the setting information corresponding to the bed ID). The operation acceptor 363 accepts the input of the control command for the bed 10 based on the operation of the operation button. The output processor 365 transmits the input control command to the bed 10 associated with the selected bed ID according to the operation of the operation button.

Thereby, the bed system 1 displays the operation buttons based on the selection of the bed ID and/or the setting information corresponding to the bed ID. Therefore, the bed system 1 can customize the display of the operation buttons for each bed 10 to be controlled. That is, the bed system 1 can customize the display of the operation buttons for each bed user based on the bed ID. Thereby, the bed system 1 can improve the operationability of the bed 10.

Also, the terminal device 30 includes the setter 364 (an example of the setter). The setter 364 generates the setting information indicating the display mode of the operation buttons. The output processor 365 displays the operation buttons in the displayer 32 in the display mode indicated by the setting information.

Thereby, the bed system 1 displays the operation buttons in the display mode (the size, the shape, the pattern, the color, and the arrangement) indicated by the setting information. Therefore, the bed system 1 can customize the display mode of the operation buttons for each bed 10 to be controlled. That is, the bed system 1 can customize the display mode of the operation buttons for each bed user. Thereby, the bed system 1 can improve the operationability of the bed 10.

Also, in the terminal device 30, the setting information is information indicating the enablement of the display of the operation buttons; and the output processor 365 displays, in the displayer 32, the operation buttons for which the display is authorized in the setting information.

Thereby, in the bed system 1, the operation buttons for which the display is authorized are displayed; and the operation buttons for which the display is prohibited are not displayed. In other words, the bed system 1 modifies the operation buttons to be displayed according to the bed 10 to be controlled. Therefore, the bed system 1 can appropriately manage the acceptable control commands for each bed 10. That is, the bed system 1 can appropriately limit and propose the control commands to be accepted for each bed user. Thereby, the bed system 1 can improve the operationability and the safety of the bed 10.

The operation acceptor 363 (an example of the modification instruction acceptor) accepts the input of the display mode modification instruction modifying the display mode of the operation buttons; and the output processor 365 modifies the display mode of the operation buttons when the display mode modification instruction is input.

Thereby, the bed system 1 modifies the display mode of the operation buttons according to the instruction of the user. Therefore, for example, even in the case where the desired operation buttons are disposed at positions that are not easy to operate in the image, the bed system 1 moves the operation buttons to positions where the operation is easy and/or makes the desired operation buttons large. Thereby, the bed system 1 can improve the operationability of the bed 10.

The operation acceptor 363 accepts the input of one control command based on the operation of multiple operation buttons; and the output processor 365 transmits the one control command that is input according to the operations of the multiple operation buttons.

Thereby, the bed system 1 requests the operations of multiple operation buttons to instruct one operation. In such a case, even when one operation button is operated, the bed system 1 does not operate the bed 10. Therefore, for example, even when the terminal user unintentionally misoperates one operation button, the bed 10 is not operated undesirably. Thereby, the bed system 1 can improve the safety of the bed 10.

The output processor 365 transmits multiple control commands according to the operation of one operation button to the bed 10 associated with the selected bed ID in the prescribed sequence.

Thereby, the bed system 1 can cause the bed 10 to perform a complex operation by the operation of one operation button. That is, it is unnecessary for the terminal user to operate the terminal device 30 multiple times to perform the same operation. Thereby, the bed system 1 can improve the convenience of the bed 10.

The output processor 365 displays the operation buttons in the displayer 32 based on the setting information corresponding to the user of the output processor 365.

Thereby, the bed system 1 displays the operation buttons based on the setting information for each terminal user. Therefore, the bed system 1 can customize the display of the operation buttons for each terminal user. Thereby, the bed system 1 can improve the operationability and the safety of the bed 10.

Second Embodiment

A second embodiment will now be described. Hereinbelow, the description is assisted by marking configurations similar to those of the first embodiment described above with the same reference numerals.

Figure 13:
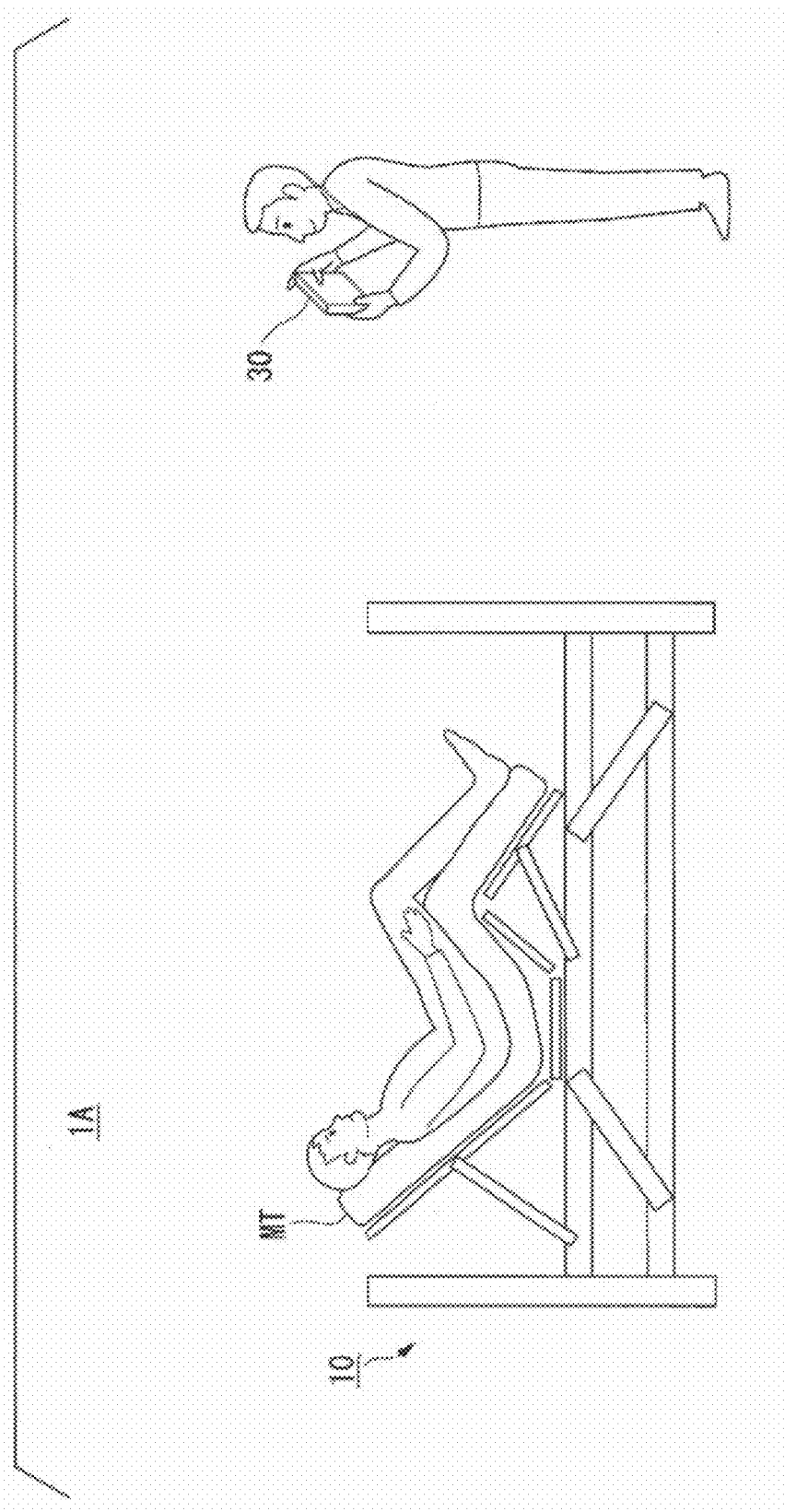
FIG. 13 is a schematic view showing an overview of a second embodiment of the invention.

FIG. 13 is a schematic view showing an overview of the embodiment.

Similarly to the bed system 1 according to the first embodiment, a bed system 1A according to the embodiment includes the bed 10 and the terminal device 30. However, the bed user and the terminal user are the same in the first embodiment; but the embodiment is different in that the bed user and the terminal user are not the same. For example, the bed user is a patient; and the terminal user is a doctor or a nurse. In such a case, because the standpoints of the bed user and the terminal user are different, the terminal device 30 displays different control screens according to the standpoint of the terminal user. Specifically, the terminal device 30 manages authority information by associating the authority information with the setting information. The authority information is information indicating the authority of the terminal user. The items of the setting information are different according to the authority information. Thereby, the terminal device 30 can control the display and the non-display of the operators and/or the display mode of the operators according to the authority of the terminal user.

Figure 14:
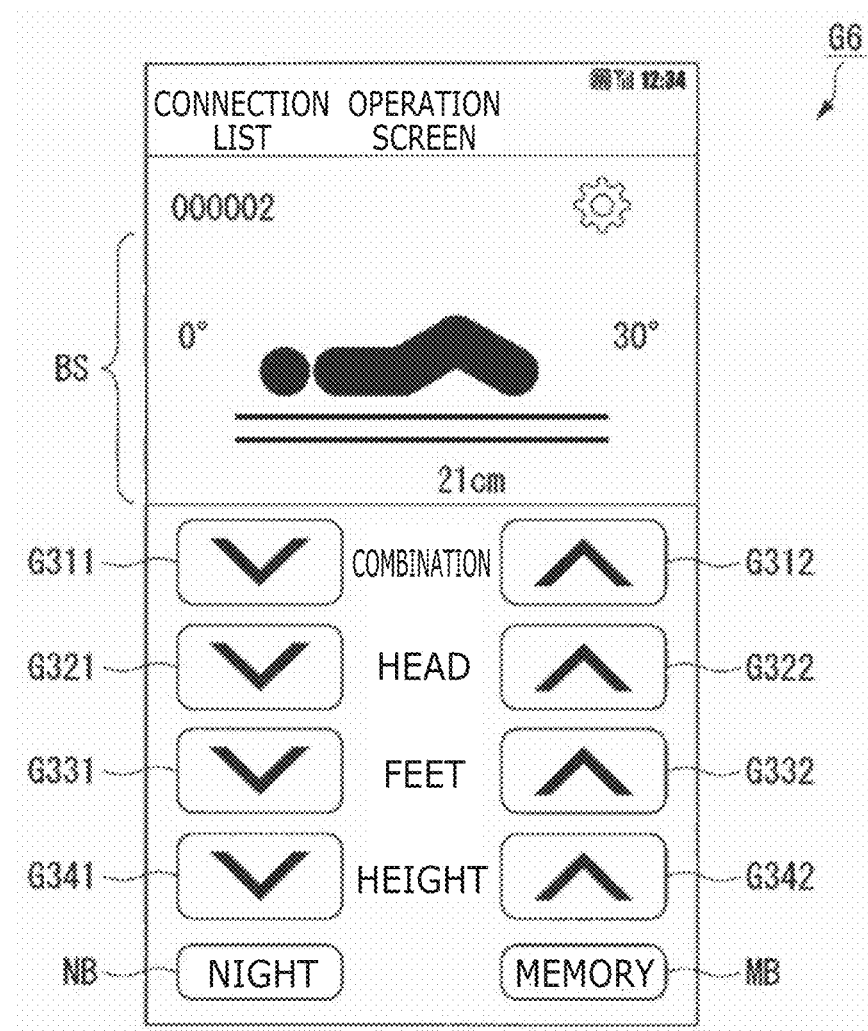
FIG. 14 is a drawing showing a control screen according to the same embodiment.

FIG. 14 is a drawing showing a control screen.

Operation buttons similar to those of the control screen G31 shown in FIG. 10 are disposed in a control screen G6 shown in FIG. 14. However, in the control screen G6, an operation button NB is disposed instead of the operation button FB. The operation button NB is an operator for night for lowering the bed height to the lowest position, setting the first rotation angle α and the second rotation angle β to zero, and setting each section of the bed 10 to the horizontal state. Thus, the terminal device 30 may add, modify, and deactivate dedicated operation buttons according to the authority of the terminal user.

In the bed system 1A as described above, the output processor 365 displays, in the displayer 32, the operation buttons based on the setting information corresponding to the authority of the user of the device of the output processor 365.

Thereby, the bed system 1A displays the operation buttons corresponding to the authority of the terminal user. Therefore, the bed system 1A can limit or authorize the utilization of the operation buttons according to the authority of the terminal user. Thereby, the bed system 1A not only can improve the operationability but also can improve the safety of the bed 10.

The authority may be determined not only according to the standpoint of the terminal user but also according to the body condition of the terminal user. For example, the authority may correspond to the degree of assistance needed.

Third Embodiment

A third embodiment will now be described. Hereinbelow, the description is assisted by marking configurations similar to those of the first described above or the second embodiment with the same reference numerals.

Figure 15:
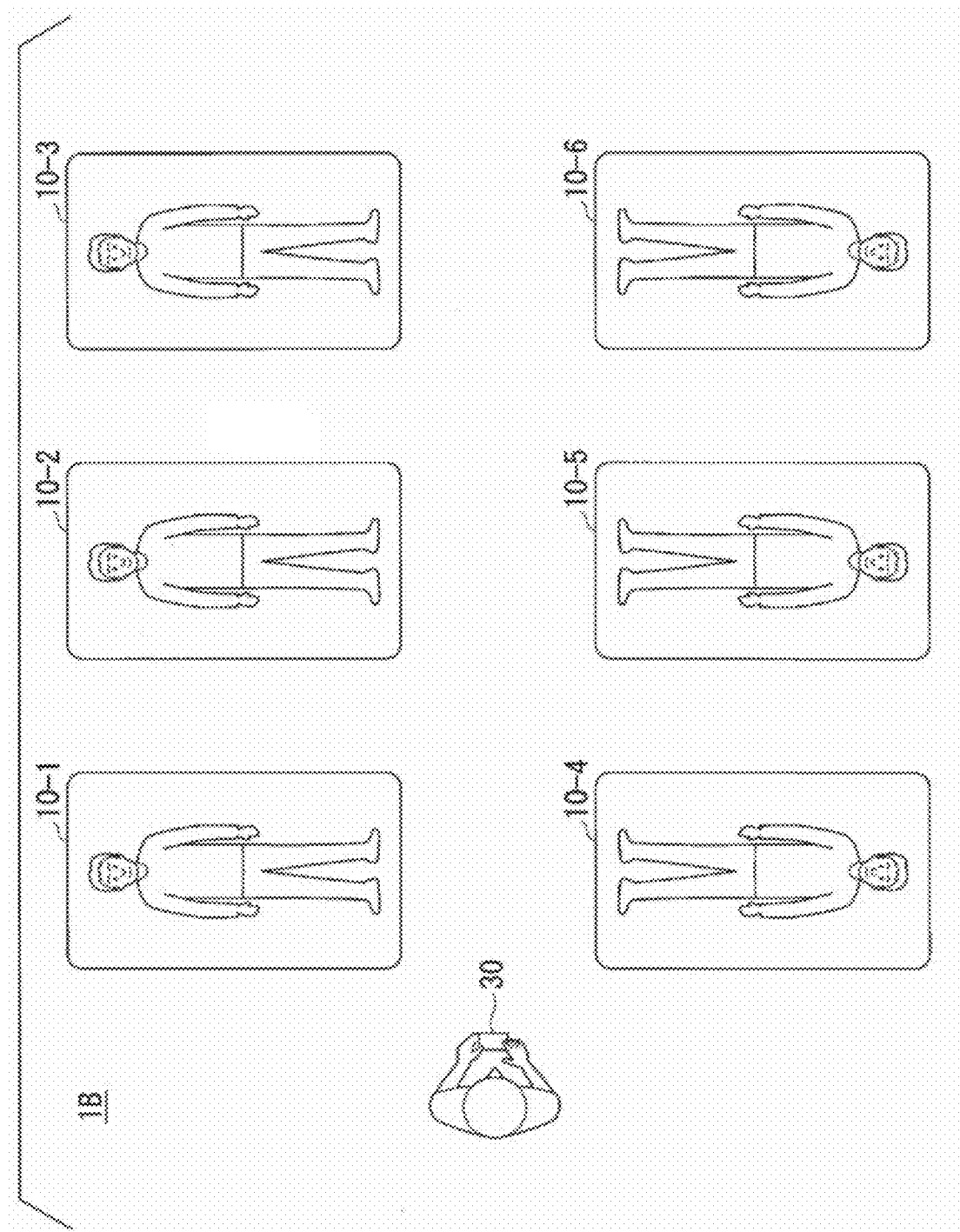
FIG. 15 is a schematic view showing an overview of a third embodiment of the invention.

FIG. 15 is a schematic view showing an overview of the embodiment.

Similarly to the bed system 1A according to the second embodiment, a bed system 1B according to the embodiment includes the bed 10 and the terminal device 30. However, one bed 10 is controllable by one terminal device 30 in the second embodiment; but the embodiment differs in that multiple beds 10 (beds 10-1, 10-2, . . . ) are controllable by one terminal device 30. Thereby, the beds 10 can be operated efficiently because it is unnecessary to input the operations of the individual beds 10 when setting the multiple beds 10 to the same state.

However, if the multiple beds 10 are controllable by one terminal device 30 without a limit, there is also an undesirable possibility that an operation inappropriate for some of the bed users may be performed. Therefore, the terminal device 30 accepts operations of the operations authorized for all of the multiple beds 10 to be controlled. Thereby, the bed system 1B not only can improve the operationability of the multiple beds 10 but also can improve the safety.

Figure 16:
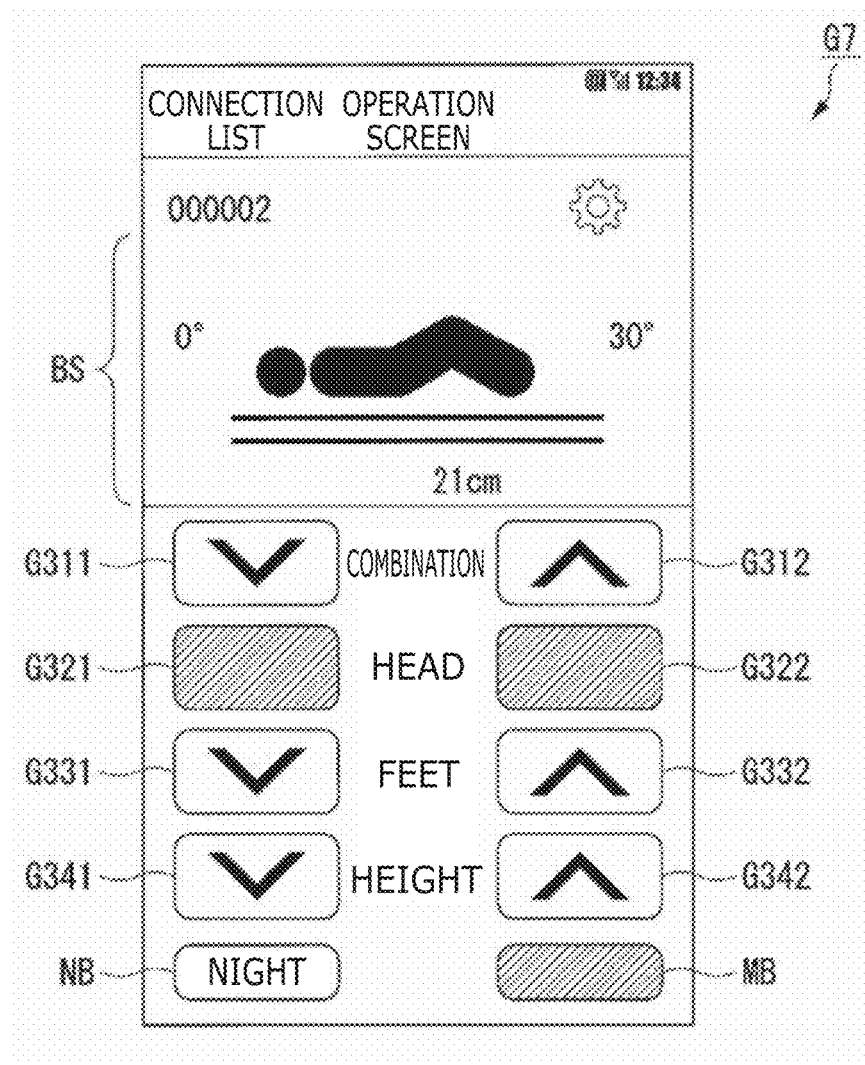
FIG. 16 is a drawing showing a control screen according to the same embodiment.

FIG. 16 is a drawing showing a control screen.

Operation buttons similar to those of the control screen G6 shown in FIG. 14 are disposed in a control screen G7 shown in FIG. 16. However, in the case where a user exists among the bed users of the multiple beds 10 to be controlled for which the modification of the first rotation angle α is prohibited, the operation buttons G321, G322, and MB are deactivated in the control screen G7. The safety of the bed 10 can be improved thereby. Also, instead of deactivating the operation buttons, the terminal device 30 may not transmit the control commands to the beds 10 utilized by the bed users for which the operations are prohibited. The information of the prohibited operations of each bed 10 or each bed user may be stored in the terminal device 30 or may be stored in the beds 10.

The display format of the control screen G6 shown in FIG. 14 also is called the first display format; and the display format of the control screen G7 shown in FIG. 16 also is called the second display format. The first display format and the second format may be switched by the terminal-side controller 36.

In the bed system 1B as described above, the output processor 365 of the terminal device 30 causes the operation buttons displayed in the displayer 32 to be different according to the number of the beds 10 to which the control commands are to be transmitted.

Thereby, in the bed system 1, the operation buttons that are displayed are different in the case where the number of the beds 10 to be controlled is different. In other words, the bed system 1 modifies the operation buttons to be displayed according to the number of the beds 10 to be controlled. For example, compared to the case of one bed 10 to be controlled, the bed system 1 limits the operation buttons to be displayed in the case of multiple beds 10 to be controlled. That is, the operations of the beds 10 are limited. Therefore, even in the case where the body condition of each bed user or the like is different, the multiple beds 10 can be operated while maintaining the safety. Thereby, the bed system 1 not only can improve the operationability of the bed 10 but also can improve the safety.

Fourth Embodiment

A fourth embodiment will now be described. Hereinbelow, the description is assisted by marking configurations similar to those of the first to third embodiments described above with the same reference numerals.

Figure 17:
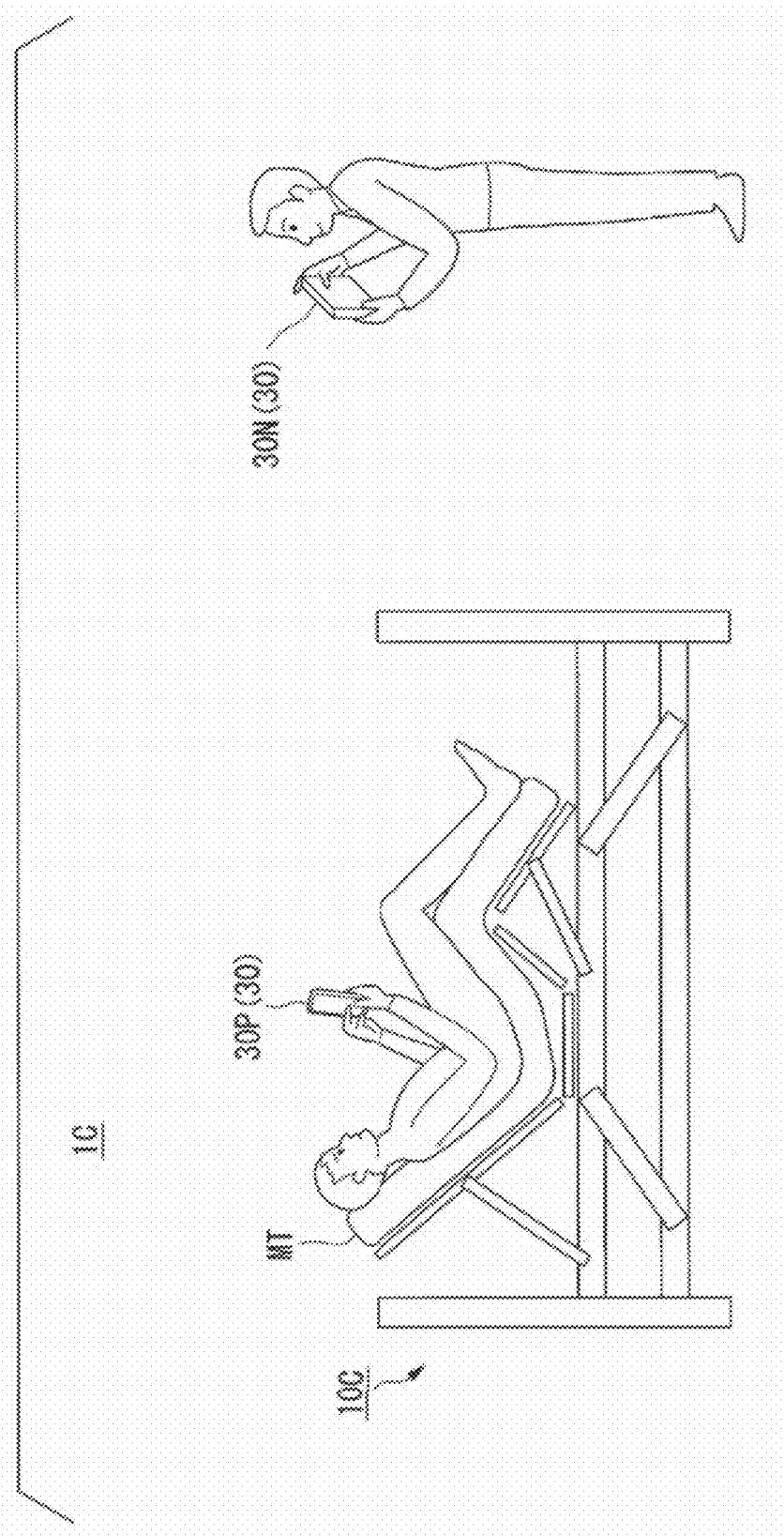
FIG. 17 is a schematic view showing an overview of a fourth embodiment of the invention.

FIG. 17 is a schematic view showing an overview of the embodiment.

Instead of the bed 10 included in the bed systems 1, 1A, and 1B described above, a bed system 1C according to the embodiment includes a bed 10C. In the embodiments described above, one terminal device 30 controls the bed 10; but the embodiment differs in that multiple terminal devices 30 that control the bed 10C exist. Thereby, the operationability can be improved because the bed 10C is operatable from the multiple terminal devices 30. In the example shown in FIG. 17, the patient which is the bed user and the nurse which is another user respectively have terminal devices 30. Hereinbelow, the terminal device 30 of the patient is called a terminal device 30P; and the terminal device 30 of the nurse is called a terminal device 30N. The patient and the nurse each have different authorities for operating the bed 10C. Here, as an example, a case is described where the nurse has a stronger authority than the patient.

Here, in the case where multiple terminal devices 30 controlling the bed 10C exist, there is also an undesirable possibility that the bed 10C may perform an unintended operation if the bed 10C equally accepts the control commands from the multiple terminal devices 30. Therefore, the bed 10C constantly limits the party having the established communication connection to one terminal device 30. For example, even when a communication connection is established with the terminal device 30P, a communication connection is established with the terminal device 30N when a connection request is received from the terminal device 30N. That is, the bed 10C gives priority to a communication connection with a terminal user having a stronger authority. Thereby, not only can the operationability of the bed 10C be improved, but also the safety of the bed 10C can be improved.

The configuration of the bed 10C will now be described.

Figure 18:
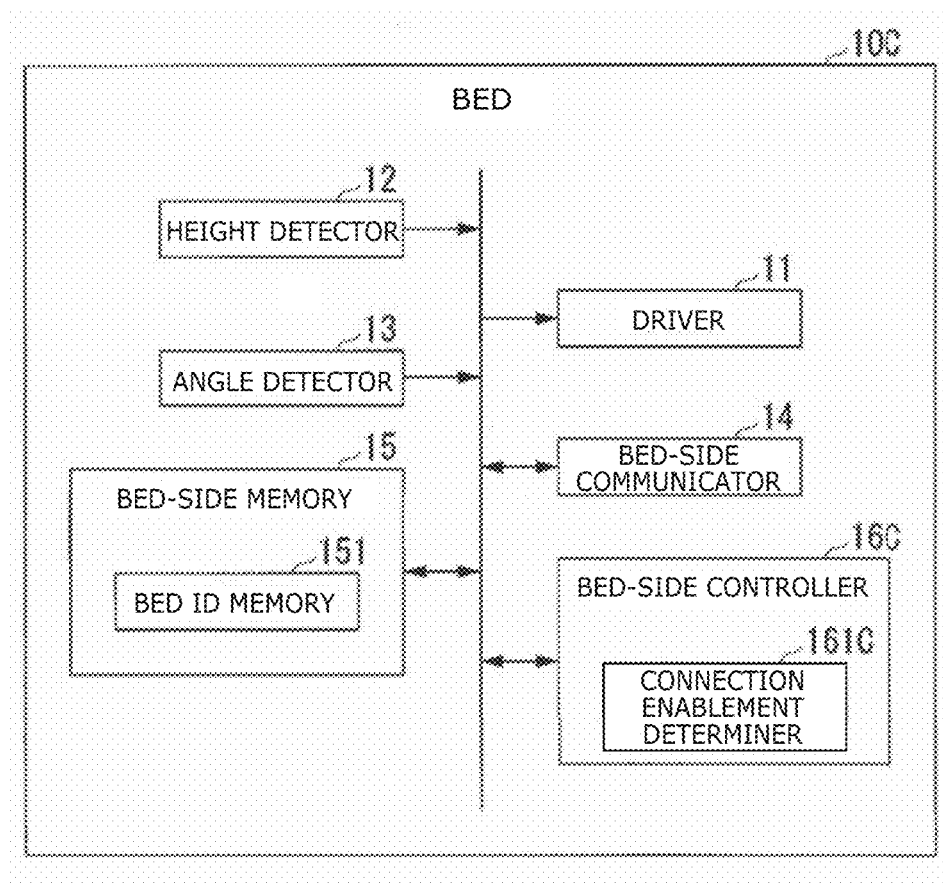
FIG. 18 is a block diagram showing the configuration of the bed according to the same embodiment.

FIG. 18 is a block diagram showing the configuration of the bed 10C.

Instead of the bed-side controller 16 included in the bed 10, the bed 10C includes a bed-side controller 16C. The bed-side controller 16C includes a connection enablement determiner 161C.

The connection enablement determiner 161O determines whether or not to establish a communication connection with a terminal device 30 when the establishment of the communication connection is requested by the terminal device 30. When a communication connection is not established with another terminal device 30, the connection enablement determiner 161C determines that a communication connection can be established with the requesting terminal device 30. Also, when a communication connection is established with another terminal device 30, the connection enablement determiner 161C compares the authorities of the terminal users between the requesting terminal device 30 and the terminal device 30 of the party with which the current communication connection is established. For example, the authority information is transmitted from the terminal device 30 when requesting the communication establishment. The connection enablement determiner 161C establishes or maintains the communication connection with the terminal device 30 of the terminal user having the stronger authority. Thereby, the connection enablement determiner 161C can limit the terminal device 30 from which the control commands are accepted according to the authorities of the terminal users and/or the condition of the communication connection.

Operations of the bed system 1C will now be described.

Figure 19:
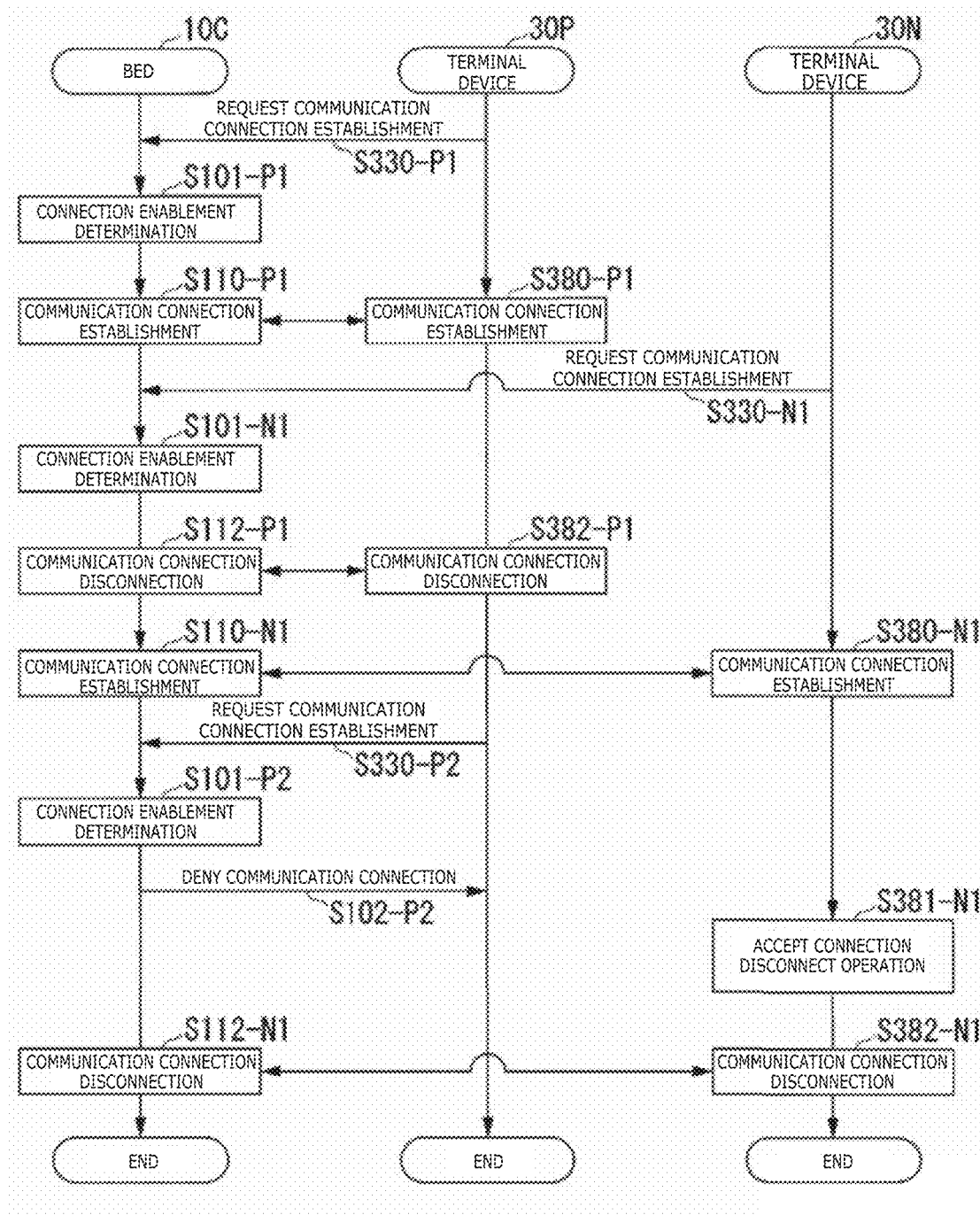
FIG. 19 is a sequence chart showing the flow of the processing by a bed system according to the same embodiment.

FIG. 19 is a sequence chart showing the operations of the bed system 1.

Here, as an example, the processing according to the establishment of the communication connection between the bed 10C and the terminal devices 30P and 30N will be described in excerpt. Also, although a designated scene is used in the description herein for convenience, the terminal device 30P and the terminal device 30N may be interchanged as appropriate according to the authorities of the terminal users. In the processing shown in FIG. 19, the reference numeral P1 indicates processing according to the first communication connection request from the terminal device 30P. Similarly, the reference numeral N1 indicates processing according to the first communication connection request from the terminal device 30N; and the reference numeral P2 indicates processing according to the second communication connection request from the terminal device 30P.

Also, a part of the processing shown in FIG. 19 is similar to the processing shown in FIG. 7. For example, the processing of steps S330-P1, S330-N1, and S330-P2 is similar to the processing of step S330. Also, the processing of steps S110-N1 and S110-P1 is similar to the processing of step S110. Also, the processing of steps S380-N1 and S380-P1 is similar to the processing of step S340.

Also, although steps S101-P1, S101-N1, and S101-P2 are similar processing, a part of the determination result is different. Also, steps S112-P1 and S112-N1 are similar processing. Also, S382-P1 and S382-N1 are similar processing.

(Step S330-P1)

The terminal device 30P requests an establishment of a communication connection with the bed 10C. Subsequently, the processing of the bed system 1C proceeds to step S101-P1.

(Step S101-P1)

For the request from the terminal device 30P, the bed 10C determines the enablement of the communication connection. Specifically, the bed 10C determines whether or not a communication connection is established with another terminal device 30. Here, because a communication connection is not established with another terminal device 30, the bed 10C determines that an establishment of a communication connection is possible. Subsequently, the processing of the bed system 1C proceeds to steps S110-P1 and S380-P1.

(Steps S110-P1 and S380-P1)

The bed 10C and the terminal device 30P establish a communication connection. Subsequently, the processing of the bed system 1C proceeds to step S330-N1.

(Step S330-N1)

The terminal device 30N requests an establishment of a communication connection with the bed 10C. Subsequently, the processing of the bed system 1C proceeds to step S101-N1.

(Step S101-N1)

For the request from the terminal device 30P, the bed 10C determines the enablement of the communication connection. Here, although the bed 10C already has established the communication connection with the terminal device 30P, the bed 10C determines to establish a communication connection with the terminal device 30N because the terminal device 30N has a stronger terminal user authority. Subsequently, the processing of the bed system 1C proceeds to steps S112-P1 and S382-P1.

(Steps S112-P1 and S382-P1)

The bed 10C disconnects the communication connection with the terminal device 30P. Subsequently, the processing of the bed system 1C proceeds to steps S110-N1 and S380-N1.

(Steps S110-N1 and S380-N1)

The bed 10C establishes a communication connection with the terminal device 30P. Subsequently, the processing of the bed system 1C proceeds to step S330-P2.

(Step S330-P2)

The terminal device 30P requests an establishment of a communication connection with the bed 10C. Subsequently, the processing of the bed system 1C proceeds to step S101-P2.

(Step S101-P2)

For the request from the terminal device 30P, the bed 10C determines the enablement of the communication connection. Here, the bed 10C determines not to establish a communication connection with the terminal device 30P because the bed 10C already has established the communication connection with the terminal device 30N and the terminal device 30N has a stronger terminal user authority. Subsequently, the processing of the bed system 1C proceeds to step S102-P2.

(Step S102-P2)

The bed 10C notifies the terminal device 30P that the communication connection is denied. Subsequently, the processing of the bed system 1C proceeds to step S381-N1.

(Step S381-N1)

The terminal device 30N accepts an operation of disconnecting the communication connection from the terminal user. Thus, the disconnection of the communication connection may be performed when explicitly instructed by the terminal user. Thereby, in the bed system 1, the safety of the bed 10C can be improved because the user of the terminal device 30N can limit the movement of the control authority of the bed 10C. Subsequently, the processing of the bed system 1C proceeds to steps S112-N1 and S382-N1.

(Steps S112-N1 and S382-N1)

The communication connection between the bed 10C and the terminal device 30P is disconnected. Subsequently, the bed system 1C ends the processing shown in FIG. 19.

In the bed system 1C as described above, the bed 10C includes the connection enablement determiner 161C (an example of the determiner) determining whether or not to accept the control command of the terminal device 30.

Thereby, the bed system 1C limits the terminal device 30 from which the bed 10 accepts control commands. That is, the terminal device 30 that can control the bed 10 is limited to one. Therefore, even in the case where multiple terminal devices 30 exist, the bed 10 does not undesirably perform an unintended operation due to control commands from the multiple terminal devices 30. Thereby, the bed system 1 not only can improve the operationability but also can improve the safety of the bed 10.

Fifth Embodiment

A fifth embodiment will now be described. Hereinbelow, the description is assisted by marking configurations similar to those of the embodiments described above with the same reference numerals.

Figure 20:
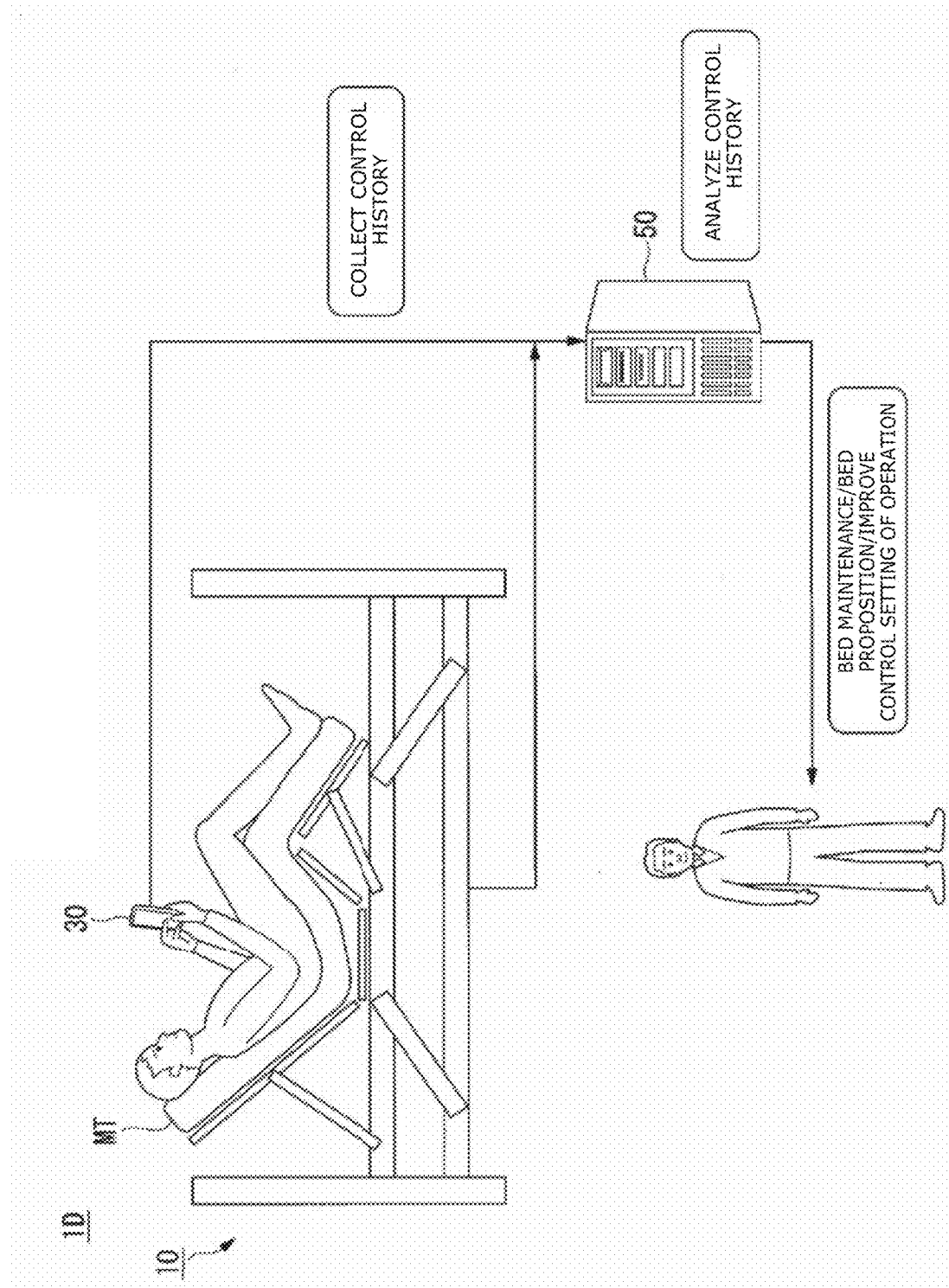
FIG. 20 is a schematic view showing an overview of a fifth embodiment of the invention.

FIG. 20 is a schematic view showing an overview of the embodiment.

Similarly to the bed systems 1 and 1A to 1C according to the embodiments described above, a bed system 1D according to the embodiment is a system including the terminal device 30 and the bed 10 or 10C. However, the bed system 1D differs in that a history analysis device 50 is further included and integrates and analyzes the control history of the bed 10 (or the bed 10C) by the terminal device 30. Although a case is described as an example hereinbelow where the bed system 1D includes the bed 10, this is similar also for the case where the bed 10C is included.

The history analysis device 50 is an electronic device that includes a computer system and is, for example, a server device. The history analysis device 50 may collect the control history from the multiple beds 10 and/or the terminal device 30. Based on the collected control history, the history analysis device 50 analyzes the utilization conditions of each bed 10, the preferences of the terminal users, the preferences of the bed users, etc. For example, the history analysis device 50 can analyze which electric actuators of the bed 10 are being utilized and how much. Also, for example, the history analysis device 50 can estimate what kind of bed 10 each bed user prefers. Also, for example, the history analysis device 50 can analyze which operations each terminal user prefers to perform. Thereby, the bed system 1D can make the maintenance of the bed 10 easy, can make a recommendation for the beds 10 and 10C, and can improve the control setting of the operations.

The configuration of the history analysis device 50 will now be described.

Figure 21:
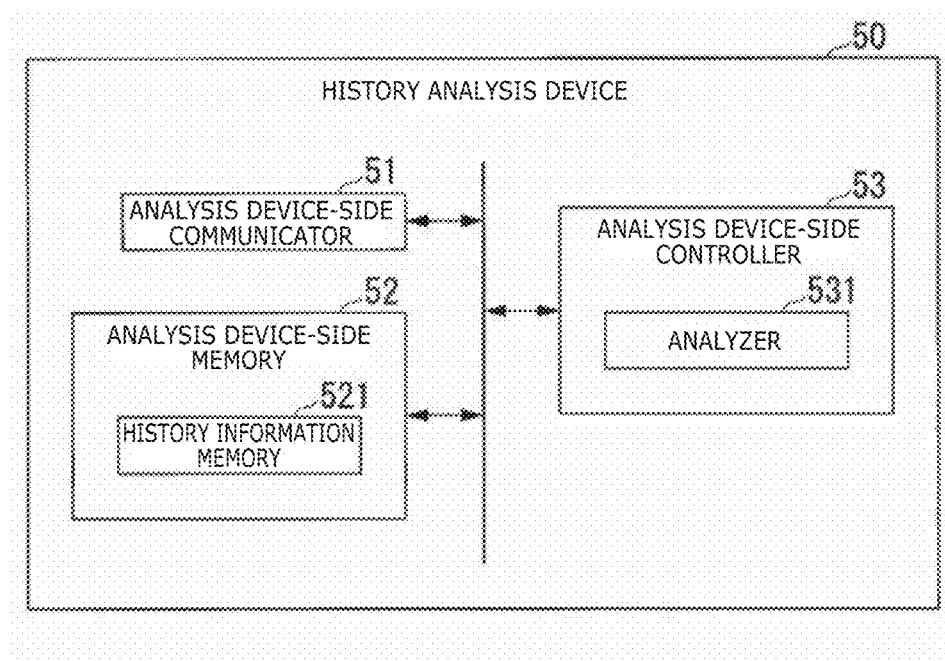
FIG. 21 is a block diagram showing the configuration of a history analysis device according to the same embodiment.

FIG. 21 is a block diagram showing the configuration of the history analysis device 50.

The history analysis device 50 includes an analysis device-side communicator 51, an analysis device-side memory 52, and an analysis device-side controller 53.

The analysis device-side communicator 51 includes, for example, a communication IC and communicates with other devices such as the terminal device 30, the bed 10, etc. The analysis device-side communicator 51 receives the communication history information from the terminal device 30 and/or the bed 10.

The analysis device-side memory 52 includes, for example, a HDD, a SSD, ROM, RAM, etc., and stores a program, various information processed by the history analysis device 50, etc. History information memory 521 is not limited to being built into the history analysis device 50 and may include an externally-attached memory device. The analysis device-side memory 52 includes the history information memory 521.

The history information memory 521 stores the history information received by the analysis device-side communicator 51. The history information is information indicating the control history of the bed 10. The data configuration of the history information is described below. By referring to the history information, the history analysis device 50 can identify when, by whom, for the bed 10 utilized by whom, what operation is input, and what type of control is performed, and as a result, to what state the bed 10 is set.

The analysis device-side controller 53 controls each component of the history analysis device 50. For example, the analysis device-side controller 53 may be realized by an arithmetic device (e.g., a CPU) included in the history analysis device 50 executing a program stored in the analysis device-side memory 52. Also, for example, the analysis device-side controller 53 may be realized as an integrated circuit such as an ASIC, etc. The analysis device-side controller 53 includes an analyzer 531.

The analyzer 531 analyzes the history information. For example, the analyzer 531 analyzes the history information for each bed ID, for each terminal user ID, and for each bed user ID.

For example, the analyzer 531 extracts the history information based on the bed ID. Then, the analyzer 531 refers to the control command information of the extracted history information and calculates, for example, the driving results of the electric actuator to date such as the drive amount, the number of drives, etc. Thereby, the analyzer 531 can analyze the likelihood of malfunction of the bed 10. Based on the analysis result, for example, the analyzer 531 may notify the terminal device 30 that a maintenance check is necessary when the driving results exceeds a prescribed threshold.

Also, for example, the analyzer 531 extracts the history information based on the terminal user ID. Then, the analyzer 531 refers to the operation button information of the extracted history information and calculates the utilization count of each operation button. Thereby, the analyzer 531 can identify the preferences of the operation buttons for each terminal user. Based on the analysis result, for example, the analyzer 531 may propose to the terminal user a control screen in which the frequently-utilized operation buttons are easy to utilize.

Also, for example, the analyzer 531 extracts the history information based on the bed user ID. Then, referring to the control result information of the extracted history information, the analyzer 531 calculates the length of time taken by this state for each state of the bed 10. Thereby, the analyzer 531 can identify the preferences of the bed 10 for each bed user. Based on the analysis result, for example, the analyzer 531 may propose the utilization of another bed 10 to the bed user. For example, the utilization of a bed 10 having a low height may be proposed to a bed user who prefers the state in which the bed height h is low.

The data configuration of the history information will now be described.

FIG. 22 is a figure showing the data configuration of the history information.

In the example shown in FIG. 22, the history information is information in which the date/time information, the terminal user ID, the bed user ID, the bed ID, the operation button information, the control command information, and the control result information are associated with each other.

The date/time information is information indicating the date/time that the terminal device 30 accepted the operation or the date/time the control command was transmitted to the bed 10. The terminal user ID is a user ID indicating the terminal user of the terminal device 30. The bed user ID is a user ID indicating the bed user of the bed 10. The operation button information is information indicating the operation button operated by the terminal user. The control command information is information indicating the control command accepted by the bed 10. The control result information is information indicating the state of the bed 10 as a control result by the terminal device 30.

As described above, the bed system 1D includes the history analysis device 50. The history analysis device 50 includes the analysis device-side memory 52 storing the history of the input control commands.

Thereby, the bed system 1D can track the control content of the bed 10. Therefore, for example, the load applied to the driver 11 of the bed 10, the utilization trend of the bed 10 for each bed user, etc., can be analyzed. Then, these analysis results can be utilized for the maintenance of the bed 10 and/or propositions to the bed user.

[Modification]

Although the embodiments of the invention are elaborated hereinabove with reference to the drawings, the specific configurations are not limited to the embodiments described above; and designs within the spirit of the invention, etc., also are included. For example, the configurations described in the first to fifth embodiments described above can be combined arbitrarily. Also, for example, the configurations described in the first to fifth embodiments described above can be omitted when unnecessary to realize the designated function. Also, the configurations described in the first to fifth embodiments described above can be included by being separated into separate devices.

In the embodiments described above, the states of the beds 10 and 10C, the content of the control command, etc., may be notified by voice. For example, a warning sound of an emergency stop may be output from the beds 10 and 10C and/or the terminal device 30.

Also, in the embodiments described above, the case is described where the beds 10 and 10C are to be controlled; but this is not limited thereto. For example, a body support apparatus that includes an electric actuator such as a wheelchair, an incubator, etc., may be the control object.

Also, the embodiments described above are described on the premise that the operations are via a touch panel; but this is not limited thereto. For example, an input device such as a mouse, a keyboard, etc., may be used in the operation input.

Also, in the embodiments described above, the terminal device 30 may acquire attribute information of the beds 10 and 10C. The attribute information of the beds 10 and 10C may include the model, the placement location, etc. The terminal device 30 may modify the setting information referred to when generating the control screen according to the attribute information. For example, by modifying the setting information according to the placement locations of the beds 10 and 10C, for example, different control screens can be displayed for each hospital room.

Also, in the embodiments described above, the beds 10 and 10C may include a sensor acquiring the biological information of the bed user. For example, the body movement, the pulse, the blood pressure, etc., may be acquired as the biological information. Also, the beds 10 and 10C may notify the terminal device 30 of the acquired biological information. Then, the terminal device 30 may limit the control commands transmitted to the beds 10 and 10C based on the biological information.

Also, in the embodiments described above, the case is described where the setting information is stored in the terminal device 30; but this is not limited thereto. For example, the setting information may be stored in a server device on a network and may be referenceable from any device. Thereby, the setting information that corresponds to one user ID is utilizable by any terminal device 30.

Figure 23:
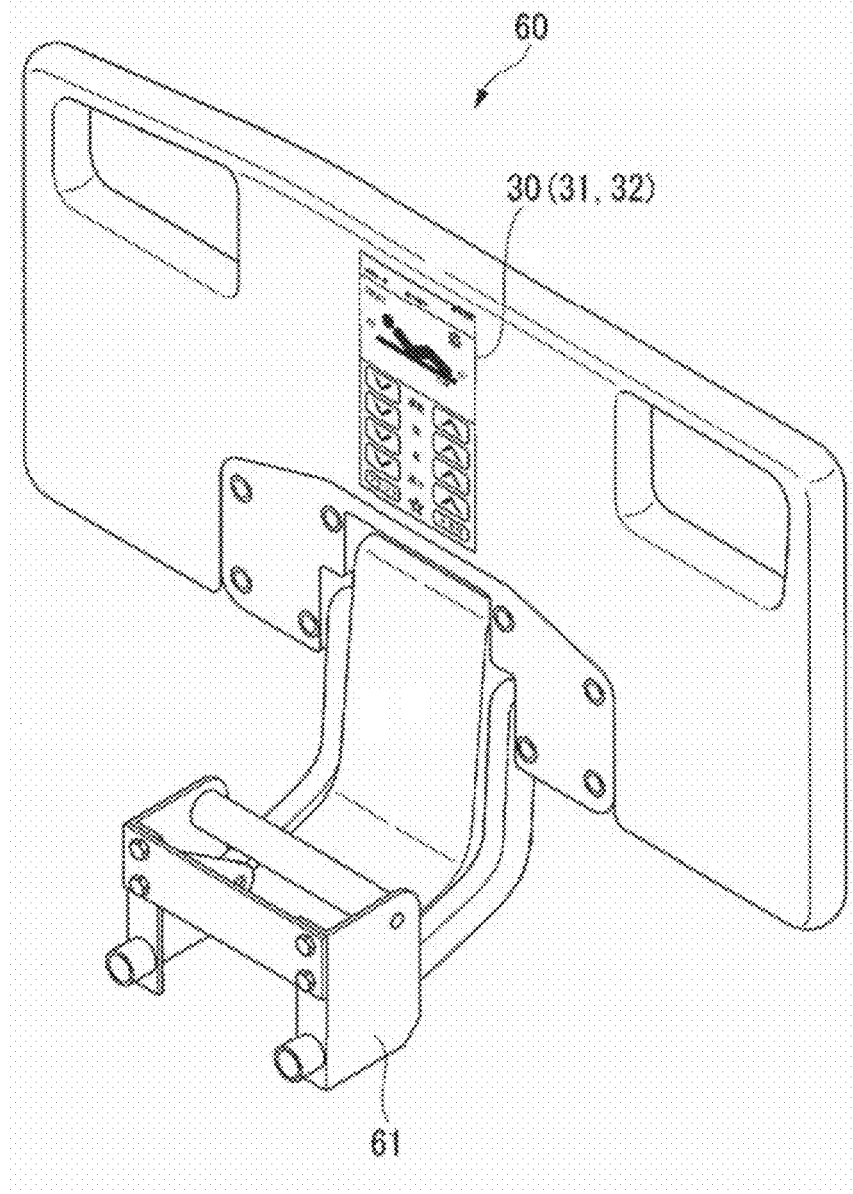
FIG. 23 is a drawing showing an example of a siderail according to a modification of the invention.

Also, in the embodiments described above, all or a part of the functions of the terminal device 30 may be performed in a siderail or a board. FIG. 23 is a drawing showing an example applied to a siderail. A siderail 60 includes a coupler 61 and is used by coupling (mounting) the coupler 61 to the side surface of the bed 10 or 10C. The inputter 31 and the displayer 32 of the terminal device 30 are embedded in the inner side (the bed side) of the siderail 60. Also, other functions of the terminal device 30 are built into the siderail 60; and the siderail 60 accepts operations from the user. Thereby, even when the user (the patient) does not have an independent terminal device 30 such as a smartphone, etc., the user (the patient) can perform operations of the beds 10 and 10C on the bed.

Also, the processing by the beds 10 and 10C, the terminal device 30, and the history analysis device 50 described above may be performed by recording, in a computer-readable recording medium, a program for realizing the functions of the beds 10 and 10C, the terminal device 30, and the history analysis device 50, by reading the program recorded in the recording medium into a computer system, and by executing the program. Here, "reading the program recorded in the recording medium into the computer system and executing" includes installing the program in the computer system. Here, the "computer system" includes hardware such as an OS, peripheral devices, etc. Also, the "computer system" may include multiple computer devices connected via a network including a communication line such as the Internet, a WAN, a LAN, a dedicated line, etc. Also, the "computer-readable recording medium" refers to a memory device such as a portable medium such as a flexible disk, a magneto-optical disk, ROM, CD-ROM, or the like, a hard disk built into a computer system, etc. Thus, the recording medium that stores the program may be a non-transitory recording medium such as CD-ROM, etc. Also, the recording medium also includes a recording medium provided externally or internally to be accessible from a distribution server for distributing the program. The code of the program stored in the recording medium of the distribution server may be different from the code of the program in the format executable by the terminal device. In other words, the format that is stored by the distribution server is arbitrary as long as it is possible to download from the distribution server and install in a format executable by the terminal device. A configuration is possible in which the program is subdivided into a plurality and combined in the terminal device after being downloaded at different timing; and the distribution servers that distribute the subdivided programs may be different. Further, the "computer-readable recording medium" also includes a medium that stores the program for a constant amount of time such as volatile memory (RAM) in the interior of a computer system used as a client or in a server in the case where the program is transmitted via a network. Also, the program recited above may be for realizing a part of the functions described above. Further, the functions described above may be a so-called difference file (difference program) that can be realized in combination with a program already recorded in the computer system.

Also, all or a part of the functions of the beds 10 and 10A, the terminal device 30, and the history analysis device 50 described above may be realized as an integrated circuit such as LSI (Large Scale Integration), etc. All or a part of the functions described above may be provided in processors individually or may be provided in a processor by integration. Also, the circuit integration technique is not limited to LSI and may be realized by a dedicated circuit or a general-purpose processor. Also, as semiconductor technology progresses and circuit integration technology emerges to replace LSI, an integrated circuit using such technology may be used.

INDUSTRIAL APPLICABILITY

According to a terminal device and a program of the invention, the operationability of a body support apparatus can be improved.

REFERENCE NUMERAL LIST 1, 1A to 1D bed systems
10, 10C beds
11 driver
12 height detector
13 angle detector
14 bed-side communicator
15 bed-side memory
16 bed-side controller
21 handy switch
22 control box
31 inputter
32 displayer
33 voice outputter
34 terminal-side communicator
35 terminal-side memory
36 terminal-side controller
50 history analysis device
51 analysis device-side communicator
52 analysis device-side memory
53 analysis device-side controller
60 siderail
61 coupler
151 bed ID memory
161C connection enablement determiner
351 terminal ID memory
352 setting information memory
361 user authenticator
362 bed ID acquirer
363 operation acceptor
364 setter
365 output processor
521 history information memory
531 analyzer

The invention claimed is:

1. A terminal device controlling a body support apparatus configured to perform a plurality of movements, the terminal device comprising:
  a displayer configured to display an operator controlling an operation of the body support apparatus, the operation being at least one of the plurality of movements; and
  a controller configured to cause the terminal device to switch between a first display mode and a second display mode based on an identified display mode in setting information, the setting information being set according to the operation of the body support apparatus and including the identified display mode, the identified display mode being the first display mode or the second display mode, the first display mode displaying a first operator and a second operator in the displayer, the first operator controlling a first movement, the second operator controlling a second movement, the second display mode displaying one of the first operator or the second operator in the displayer.

2. The terminal device according to claim 1, wherein the controller is configured to cause the terminal device to,
accept a selection of the body support apparatus,
display, in the displayer, an operator corresponding to the selected body support apparatus, and
based on an operation of the operator, accept an input of a control command for the body support apparatus and transmits the control command to the selected body support apparatus according to the operation of the operator.

3. The terminal device according to claim 2, wherein the controller is configured to cause the terminal device to,
acquire identification information associated with the body support apparatus,
accept a selection of the identification information,
based on the identification information, display the operator in the displayer, and
transmit the control command to the body support apparatus associated with the selected identification information.

4. The terminal device according to claim 1, wherein the controller is configured to cause the terminal device to,
generate the setting information, the setting information indicating a display mode of the operator, and
display, in the displayer, the operator in the display mode indicated by the setting information.

5. The terminal device according to claim 1, wherein the controller is configured to cause the terminal device to,
generate the setting information, the setting information indicating an enablement of the display of the operator, and
display, in the displayer, the operator authorized in the setting information to be displayed.

6. The terminal device according to claim 1, wherein the controller is configured to cause the terminal device to,
accept an input of a display mode modification instruction of modifying a display mode of the operator, and
modify the display mode of the operator when the display mode modification instruction is input.

7. The terminal device according to claim 1, wherein the controller is configured to cause the terminal device to,
accept an input of one control command for the body support apparatus based on a plurality of operations of the operator, and
transmit the one control command according to the plurality of operations of the operator.

8. The terminal device of claim 1, wherein the operator controls the operation of the body support apparatus upon an action by the user on the operator.

9. A program causing a computer to execute, the computer being of a terminal device configured to control a body support apparatus capable of a plurality of movements, the program causing the computer to execute:
displaying an operator controlling an operation of the body support apparatus, the operation being at least one of the plurality of movements; and
switching between a first display mode and a second display mode based on an identified display mode in setting information, the setting information being set according to the operation of the body support apparatus and including the identified display mode, the identified display mode being the first display mode or the second display mode, the first display mode displaying a first operator and a second operator, the first operator controlling a first movement, the second operator controlling a second movement, the second display mode displaying one of the first operator or the second operator.

10. The terminal device according to claim 1, wherein the setting information includes at least one of head speed information, height speed information, combination enablement information, head operation enablement information, foot operation enablement information, height operation enablement information or bed-exit notification enablement information.

11. The program according to claim 9, wherein the setting information includes at least one of head speed information, height speed information, combination enablement information, head operation enablement information, foot operation enablement information, height operation enablement information or bed-exit notification enablement information.

12. The program of claim 9, wherein the operator controls the operation of the body support apparatus upon an action by the user on the operator.

* * * * *